(12) United States Patent
Makris et al.

(10) Patent No.: US 6,689,564 B2
(45) Date of Patent: Feb. 10, 2004

(54) MUTATIONS IN IKKγ

(75) Inventors: Konstantinos Makris, San Diego, CA (US); Michael Karin, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/882,507

(22) Filed: Jun. 15, 2001

(65) Prior Publication Data

US 2002/0056150 A1 May 9, 2002

Related U.S. Application Data

(60) Provisional application No. 60/212,438, filed on Jun. 16, 2000.

(51) Int. Cl.$^7$ ............................ C12Q 1/68; C12P 21/06; C12N 15/00; C07H 21/02; C07H 21/04
(52) U.S. Cl. ........................ 435/6; 435/69.1; 435/194; 435/320.1; 435/325; 536/23.2; 536/23.1
(58) Field of Search ..................... 435/6, 194, 320.1, 435/325, 69.1; 536/23.2

(56) References Cited

U.S. PATENT DOCUMENTS

| | | | |
|---|---|---|---|
| 4,683,195 A | 7/1987 | Mullis | 435/6 |
| 4,683,202 A | 7/1987 | Mullis | 435/91 |
| 4,965,188 A | 10/1990 | Mullis | 435/6 |
| 2003/0032055 A1 | 2/2003 | Kenwrick et al. | 435/7.1 |

OTHER PUBLICATIONS

Asea et al., "HSP70 stimulates cytokine production through a CD14–dependant pathway, demonstrating its dual role as a chaperone and cytokine," *Nat. Med.* 6:435–442 [2000].
Ausubel et al. (eds.), *Current Protocols in Molecular Biology*, John Wiley & Sons, Inc., New York [1994]List of contents.
Barnes and Karin, "Nuclear factor–78 B—a pivotal transcription factor in chronic inflammatory diseases," *New Engl. J. Med.* 336:1066–1071 [1997].
Beg et al., "Embryonic lethality and liver degeneration in mice lacking the RelA component of NK–κB," *Nature* 376:167–170 [1995].
Beg and Baltimore, "An essential role for NK–κB in preventing TNF–α–induced cell death," *Science* 274:782–784 [1996].
Carney, "Incontinentia pigmenti: a world statistical analysis," *Arch. Dermatol.* 112:535–542 [1976].
Chen et al., "Long–range sequence analysis in Xq28: thirteen known and six candidate genes in 219.4 kb of high GC DNA between the *RCP/GCP* and *G6PD* loci," *Hum. Mol. Genet.* 5:659–668 [1996].
DiDonato et al., "A cytokine–responsive IκB kinase that activates the transcription factor NK–κB ," *Nature* 388:548–554 [1997].

Fard and Goldberg, "Persistence of fetal vasculature in the eyes of patients with incontinentia pigmenti," *Arch. Ophthalmol.* 116:682–684 [1998].
Feng et al., "Interleukin–1α stimulates KC synthesis in rat mesangial cells: glucocorticoids inhibit KC induction by IL–1," *Am. J. Physiol.* 266:713–722 [1994].
Francis and Sybert, "Incontinentia pigment," *Semin. Cutan. Med. Surg.* 16:54–60 [1997].
Ganguly et al., "Conformation–sensitive gel electrophoresis for rapid detection of single–base differences in double–stranded PCR products and DNA fragments: evidence for solvent–induced bends in DNA heteroduplexes," *Proc. Natl. Acad. Sci. USA* 90:10325–10329 [1993].
Ghosh et al., "NF–κB and rel proteins: evolutionarily conserved mediators of immune responses," *Ann. Rev. Immunol* .16:225–260 [1998].
Hu et al., "Abnormal morphogenesis but intact IKK activation in mice lacking the IKKα subunit of IκB kinase," *Science* 284:316–320 [1999].
Jin and Jeang, "Isolation of full–length cDNA and chromosomal localization of human NF–κB modulator NEMO to Xq28," *J. Biomed. Sci.* 6:115–120 [1999].
Landy and Donnai, Incontinentia pigmenti (Bloch––Sulzberger syndrome) *J. Med. Genet.* 30:53–59 [1993].
Li et al., "Identification of a cell protein (FIP–3) as a modulator of NK–κB activity and as a target of an adenovirus inhibitor of tumor necrosis factor α–induced apoptosis," *Proc. Natl. Acad. Sci. USA* 96:1042–1047 [1999].
Li et al., "IKK1–deficient mice exhibit abnormal development of skin and skeleton," *Genes Dev.* 13:1322–1328 [1999].
Liu et al., "Dissection of TNF receptor 1 effector functions: JNK activation is not linked to apoptosis while NK–κB activation prevents cell death," *Cell* 87:565–576 [1996].
Ma et al., "Transcriptional control of K5, K6, K14, and K17 keratin genes by AP–1 and NF–κB family members," *Gene Expr.* 6:361–370 [1997].
Machado–Pinto, "Eosinophilic and neutrophilic spongiosis: clues to the diagnosis of immunobullous diseases and other inflammatory disorders," *Semin. Cutan. Med. Surg* . 15:308–316 [1996].
Makris et al., "Female mice heterozygous for IKKγ/NEMO deficiencies develop a dermatopathy similar to the human X–linked disorder incontinentia pigmenti," *Mol. Cell* 5:969–979 [2000].

(List continued on next page.)

*Primary Examiner*—Maryam Monshipouri
(74) *Attorney, Agent, or Firm*—Medlen & Carroll LLP

(57) ABSTRACT

The present invention relates to compositions and methods involving IKKγ mutants. In particular, the present invention provides methods and compositions, including transgenic animals, suitable for use in determining means to treat, control, and/or prevent incontinentia pigmenti (IP). The present invention also provides methods to detect the presence of mutations in the IKKγ gene and protein.

35 Claims, 19 Drawing Sheets

(8 of 19 Drawing Sheet(s) Filed in Color)

OTHER PUBLICATIONS

Mercurio et al., "IKK-1 and IKK-2: Cytokine-activated IκB kinases essential for NF-κB activation," *Science* 278:860–866 [1997].

Nagy et al., "Derivation of completely cell culture-derived mice from early passage embryonic stem cells," *Proc. Natl. Acad. Sci. USA* 90:8424–8428 [1993].

Ohashi et al., "Cutting edge: heat shock protein 60 is a putative endogenous ligand of the toll-like receptor-4 complex," *J. Immunol.* 164:558–561 [2000].

Orita et al., "Rapid and sensitive detection of point mutations and DNA polymorphisms using the polymerase chain reaction," *Genomics* 5:874–879 [1989].

Régnier et al., "Identification and characterization of an IκB kinase," *Cell* 90:373–383 [1991].

Roberts et al., "Incontinentia pigmenti in a newborn male infant with DNA confirmation," *Am. J. Med. Genet.* 75:159–163 [1998].

Rothwarf et al., "IKK-γ is an essential regulatory subunit of the IκB kinase complex," *Nature* 395:297–300 [1998].

Rothwarf and Karin, "The NF-κB activation pathway: a paradigm in information transfer from membrane to nucleus," *Science's STKE* [1999].

Rudolph et al., "Severe liver degeneration and lack of NF-κB activation in NEMO/IKKγ-deficient mice," *Genes Dev.* 14:854–862 [2000].

Scheuerle, "Male cases of incontinentia pigmenti: case report and review," *Am. J. Med. Genet.* 77:201–218 [1998].

Sefiani, et al., "The gene for incontinentia pigmenti is assigned to X928," *Genomics* 4:427–429 [1989].

Seitz et al., "Alterations in NF-κB function in transgenic epithelial tissue demonstrate a growth inhibitory role for NF-κB," *Proc. Natl. Acad. Sci. USA* 95:2307–2312 [1998].

Smahi et al.,"Genomic rearrangement in *NEMO* impairs NF-κB activation and is a cause of incontinentia pigmenti," *Nature* 405:466–472 [2000].

Southern, "Detection of specific sequences among DNA fragments separated by gel electrophoresis," *J. Mol. Biol.* 98:503–517 [1975].

Takeda et al., "Limb and skin abnormalities in mice lacking IKKα," *Science* 284:313–316 [1999].

Tanaka et al., "Embryonic lethality, liver degeneration, and impaired NF-κB activation in IKK-β-deficient mice," *Immunity* 10:421–429 [1999].

Thomas, "Hybridization of denatured RNA and small DNA fragments transferred to nitrocellulose," *Proc. Natl. Acad. Sci. USA* 77:5201–5205 [1980].

Van Antwerp et al., "Suppression of TNF-α-induced apoptosis by NF-κB," *Science* 274:787–789 [1996].

Wang et al., "TNF- and cancer therapy-induced apoptosis: Potentiation by inhibition of NF-κB," *Science* 274:784–787 [1996].

Westphal and Leder, "Transposon-generated 'knock-out' and 'knock-in' gene-targeting constructs for use in mice," *Curr. Biol.* 7:530–533 [1997].

Wettke-Scahfer and Kantner, "X-linked dominant inherited diseases with lethality in hemizygous males," *Hum. Gente.* 64:1–23 [1983].

Yamaoko et al., "Complementation cloning of NEMO, a component of the IκB kinase complex essential for NF-κB activation," *Cell* 93:1231–1240 [1998].

Zandi et al., "The IκB kinase complex (IKK) contains two kinase subunits, IKKα, and IKKβ, necessary for IκB phosphorylation and NF-78 B activation," *Cell* 91:243–252 [1997].

Zandi et al., "Direct phosphorylation of IκB by IKKα and IKKβ: Discrimination between free and NF-κB-bound substrate," *Science* 281:1360–1363 [1998].

Aradhya et al., "A recurrent deletion in the ubiquitously expressed *NEMO* (IKK-γ) gene accounts for the vast majority of incontinentia pigmenti mutations," *Hum. Mol. Genet.* 10:2171–2179 [2001].

Aradhya et al., "Atypical forms of incontinentia pigmenti in male individuals result from mutations of acytosine tract in exon 10 of *NEMO (IKK-y),*" *Am. J. Hum. Genet.* 68:765–771 [2001].

International IP Consortium, "Survival of male patients with incontinentia pigmenti carrying a lethal mutation can be explained by somatic mosaicism or klinefelter syndrome," *Am. J. Hum. Genet.* 69:000–000 [2001].

Kosaki et al., "Female patients showing hypohidrotic ectodermal dysplasia and immunodeficiency (HED–ID)," *Am. J. Hum. Genet.* 69:664–665 [2001].

Schmidt-Ullrich et al., "Requirement of NF-κB/rel for the development of hair follicles and other epidermal appendices," *Development* 128:3843–3853 [2001].

Zonana et al., "A novel x-linked disorder of immune deficiency and hypohidrotic ectodermal dysplasia is allelic to incontinentia pigmenti and due to mutations in *IKK–gamma (NEMO),*" *Am. J. Hum. Genet.* 67:1555–1562 [2000].

Smahi et al. (2000) "Genomic rearrangement in *NEMO* impairs NF-κB activation and is a cause of incontinentia pigmenti," *Nature* 405:466–472 (May 25, 2000 issue).

NORMAL SEQ    AGG AGC CCC CCC GAG GAG CCA CCT GAC TTC ...
NORMAL PROT    R   S   P   P   E   E   P   P   D   F

IP SEQ    AGG AGC CCC CCC GAG GAG CCA CCC CGA GGA GCC ACC TGA
IP PROT    R   S   P   P   E   E   P   P   R   G   A   T  STOP

FIG. 12C

MUTATIONS IN IKKγ

CROSS-REFERENCE TO RELATED APPLICATIONS

This application for a regular U.S. Utility Application claims priority to, and perfects the filing date of, Provisional U.S. Patent Application serial No. 60/212,438 filed on Jun. 16, 2000.

STATEMENT AS TO RIGHTS TO THE INVENTION

This invention was made, in part, with Government support by the National Institutes of Health Grant Numbers E504151 and AI43477. The Government has certain rights in the invention.

FIELD OF THE INVENTION

The present invention relates to compositions and methods involving IKKγ and IKKγ mutants. In particular, the present invention provides methods and compositions, including transgenic animals, suitable for use in determining means to treat, control, and/or prevent incontinentia pigmenti (IP). The present invention also provides methods to detect the presence of mutations in the IKKγ gene and protein.

BACKGROUND OF THE INVENTION

Incontinentia pigmenti (IP), an X-linked human genodermatosis is a relatively rare disorder associated with multiple congenital defects (Landy and Donnai, *J. Med. Genet.* 30:53–59 [1993]; and Francis and Sybert, *Semin. Cutan. Med. Surg.* 16:54–60 [1997]), the gene of which (IP) has been mapped to Xq28 (Sefiani et al., *Genomics* 4:427–429 [1989]; and Sefiani et al., *Human. Genet.* 86:297–299 [1991]). Because of Lyonization, IP occurs almost exclusively in females, as most affected males die pre- and perinatally, unless their karyotype is 47XXY (Landy and Donnai, supra [1993]; Francis and Sybert, supra [1997]; and Scheuerle, *Am. J. Med. Genet.* 77:201–218 [1998]). The characteristic features of IP are detected at or soon after birth. These features commonly begin with an erythematous eruption of the skin, with linear vesiculation. The blistering stage progresses to the verrucous stage, in which multiple longitudinal verrucous lesions are distributed along the skin. Within a year, these hyperkeratotic lesions disappear and leave behind the classic hyperpigmented whorls and streaks, which may fade later in life. The name of the disease is derived from the characteristic finding that these dark lines and swirls are due to loss (incontinence) of melanin from basal keratinocytes and its deposition as free pigment or within dermal macrophages (i.e., melanophages). The first three stages of the disease occasionally overlap. Eventually, many of the cutaneous symptoms disappear and the disease in adult females (i.e., subjects who can pass the disease along to their progeny) is characterized by irregular, pale, hairless, anhidrotic streaks and splashes of hyperpigmentation, resulting in a "marble cake" pattern (Wettke-Scahfer and Kantner, *Hum. Genet.* 64:1–23 [1983]; Landy and Donnai, supra [1993]; and Francis and Sybert, supra [1997]).

Although this disease is rare, the significant morbidity and mortality associated with IP indicate the need to develop methods to treat and prevent the disease.

SUMMARY OF THE INVENTION

The present invention relates to compositions and methods involving both wild type and mutant IκB kinase-γ (IKKγ) genes and proteins. In particular, the present invention provides methods and compositions, including transgenic animals, suitable for use in determining means to treat, control, and/or prevent the genodermatosis, incontinentia pigmenti (IP).

IKKγ, also known as the nuclear factor-κB (NF-κB) essential modulator or NEMO, is the essential regulatory subunit of the IκB kinase (IKK) and is encoded by an X-linked gene in mice and humans. It is required for NF-κB activation and resistance to tumor necrosis factor (TNF)-induced apoptosis. Female mice heterozygous for IKKγ/NEMO deficiency develop unique dermatopathy, characterized by keratinocyte hyperproliferation, skin inflammation, hyperkeratosis, and increased apoptosis. Although Ikkγ$^{+/-}$ females eventually recover, Ikkγ$^-$ males die in utero. These symptoms and inheritance pattern are very similar to those of IP, a human genodermatosis that is syntenic with the IKKγ/NEMO locus. Indeed, biopsies and cells from IP patients exhibit defective IKKγ/NEMO expression, but normal expression of IKK catalytic subunits. This unique self-limiting disease, the first to be genetically linked to the IKK signaling pathway, is dependent upon X-chromosome inactivation. Although an understanding of the mechanism (s) is not necessary in order to use the present invention, the results obtained during the development of the present invention indicate that IKKγ/NEMO-deficient cells trigger an inflammatory reaction that eventually leads to the death of these cells.

The present invention provides transgenic nonhuman animals having a genome comprising a disruption of the endogenous Ikkγ/NEMO gene, which is a result of the insertion of a transgene and which causes a decrease in IKKγ/NEMO expression. In some embodiments, IKKγ/NEMO expression is eliminated. In a preferred embodiment, the transgenic nonhuman animal is a mouse bearing a heterozygous disruption of the Ikkγ/NEMO gene. In some embodiments, the transgenic mouse exhibits hypersensitivity to TNFα-induced apoptosis, while in other embodiments, the transgenic mouse exhibits dermatopathy, keratinocyte hyperproliferation, skin inflammation and/or hyperkeratosis.

The present invention further provides cells derived from a transgenic nonhuman animal having a genome comprising a disruption of the endogenous Ikkγ/NEMO gene, wherein the disruption is a result of the insertion of a transgene. In particularly preferred embodiments, the disruption results in a decrease in IKKγ/NEMO expression. In one preferred embodiment, the cell is derived from a transgenic mouse bearing a heterozygous disruption of the Ikkγ/NEMO gene. In some embodiments, the cell is an embryonic stem cell, while in other embodiments, the cell is selected from the group consisting of embryonic fibroblasts, hepatocytes, thymocytes, splenocytes and epidermal cells. In some preferred embodiments, the cell exhibits hypersensitivity to TNFα-induced apoptosis.

The present invention also provides methods for screening for biologically active agents to treat incontinentia pigmenti. These methods comprise: (a) exposing a transgenic mouse having a genome comprising a disruption of the endogenous Ikkγ/NEMO gene, which is a result of the insertion of a transgene and which causes a decrease in IKKγ/NEMO expression to a candidate agent; and (b) determining the effect of the candidate agent on incontinentia pigmenti pathology. In some embodiments, assessment of the effect of the candidate agent on incontinentia pigmenti pathology is accomplished by measuring sensitivity to TNFα-induced apoptosis, while in other embodiments the degree of dermatopathy, keratinocyte hyperproliferation and/or skin inflammation is assessed.

The present invention also provides methods for detecting mutant Ikkγ/NEMO genes in biopsy material obtained from individuals. These methods comprise detecting IKKα and IKKβ expression, in the absence of IKKγ/NEMO expression. In some embodiments, detection is by immunoblot, while in others it is by Northern blot, Southern blot, reverse transcription-polymerase chain reaction (RT-PCR), single-stranded conformation polymorphism (SSCP) analysis and/or conformation-sensitive gel electrophoresis (CSGE).

DESCRIPTION OF THE FIGURES

The file of this patent contains at least one drawing executed in color. Copies of this patent with color drawing (s) will be provided by the Patent and Trademark Office upon request and payment of the necessary fee.

FIGS. 12A–C shows a mutation analysis of Ikkγ exon 10 by conformation sensitive gel electrophoresis (CSGE). Panel A provides a schematic of the human IP family examined as described in Example 11. Panel B shows the CSGE gel containing Ikkγ exon 10 fragments, PCR-amplified from: (1) a female IP carrier, (2) her normal son, (3) a wild type fibroblast line, and (4) an IP fibroblast line. Panel C depicts a portion of the wild type Ikkγ exon 10 gene sequence (SEQ ID NO:7) and the corresponding IKKγ protein sequence (SEQ ID NO:8), as compared to the IP patient's mutant Ikkγ exon 10 gene sequence (SEQ ID NO:9) and the corresponding mutant IKKγ protein sequence (SEQ ID NO:10).

DEFINITIONS

Figure 1A:
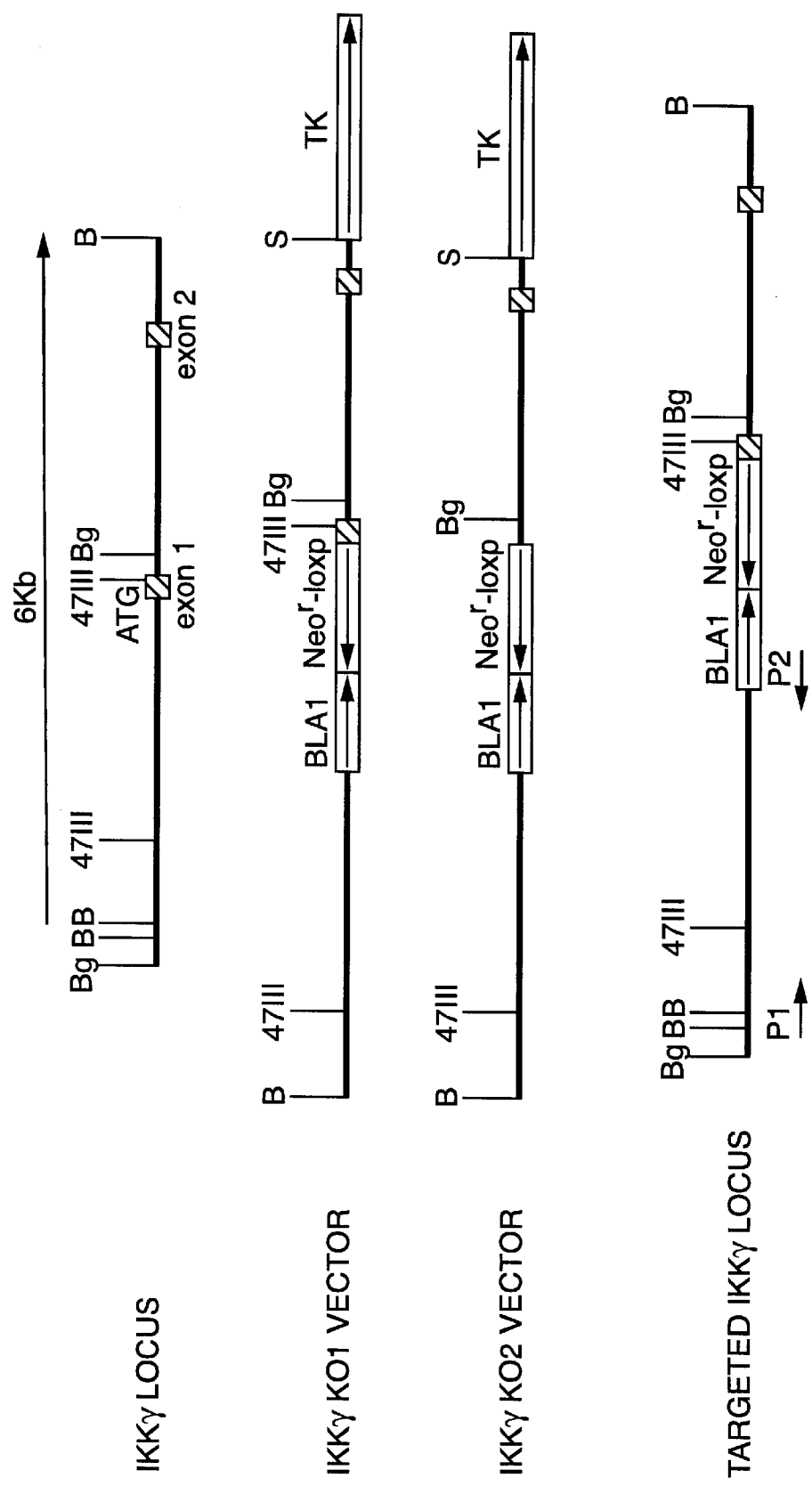
FIGS. 1A–1E show various aspects involved in the generation of IKKγ/NEMO-deficient mice. In Panel A, maps of the mouse Ikkγ/NEMO locus, targeting vectors, and the targeted allele generated by homologous integration of vector 1 are provided. In this Figure, exons 1 and 2 are indicated by the solid boxes. The translation start site, selection markers, hybridization probe (bold line), PCR screening primers (P1 and P2), and restriction enzyme sites are shown (B, BamHI; Bg, Bg/II; 47III, Eco47III; S, SalI). Panel B provides the results of Western blot analysis of IKK subunits in whole embryonic stem (ES) cell extracts. In this Figure, lane 1 contains wild-type, lane 2 contains Ikkγ$^-$ from KO1, lane 3 contains Ikkγ$^-$ ES2 from KO1, lane 4 contains Ikkγ$^-$ ES3 from KO2, and lane 5 contains Ikkγ$^-$ ES4 from KO2; IKKγ(N) and IKKγ(C) refer to antibodies directed against the N- and C-terminal regions of IKKγ/NEMO, respectively. Panel C provides results of experiments in which murine embryonic fibroblasts (MEFs) derived from wild-type and Ikkγ$^-$ E12 embryos were treated with 10 ng/ml tumor necrosis factors (TNFα) or 20 ng/ml interleukin-1 (IL-1). At the indicated times, cells were lysed and IKK activity (KA) was measured by immune complex kinase assay using IKKα antibodies and glutathione-s-transferase fusion protein, GST-1κBα (1-54), as a substrate. The reaction products were separated by a 10% SDS-PAGE, transferred to a membrane, and autoradiographed. The membrane was reprobed (Blot: IKKα) with a monoclonal antibody against IKKα as a loading control. Panel D shows the NF-κB binding activity in 20 μg of whole cell extracts prepared as described in Example 3. NF-1 probe binding was used to control the quality and quantity of the nuclear protein extract. Panel E illustrates TNFα-induced cytotoxicity for wild-type and Ikkγ MEFs treated with mouse TNFα (50 ng/ml). At the indicated time points, cells were fixed, stained with DAPI, and mounted with a coverslip. Values shown are percentages of apoptotic nuclei scored using a fluorescent microscope.
Figure 1B:
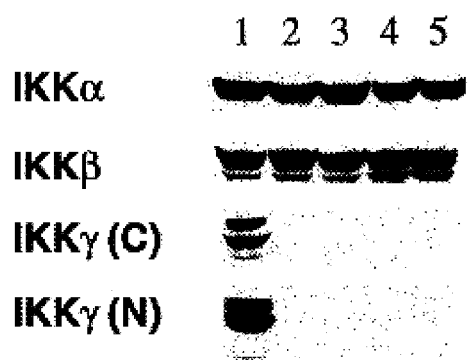
Figure 1C:
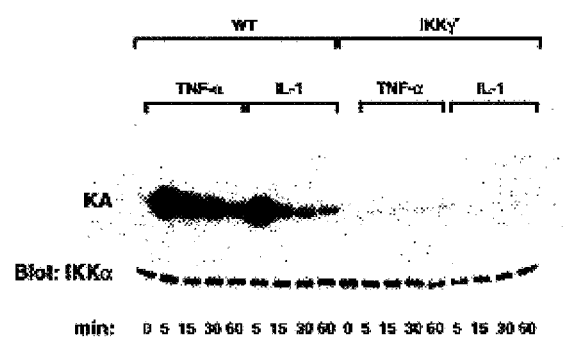
Figure 1D:
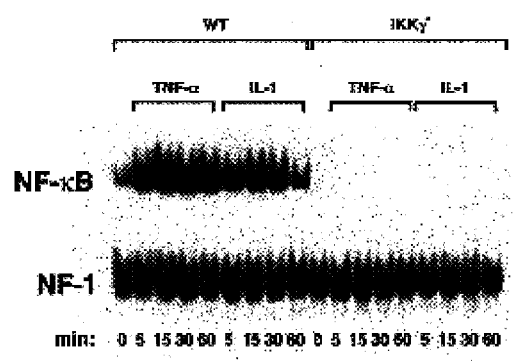
Figure 1E:
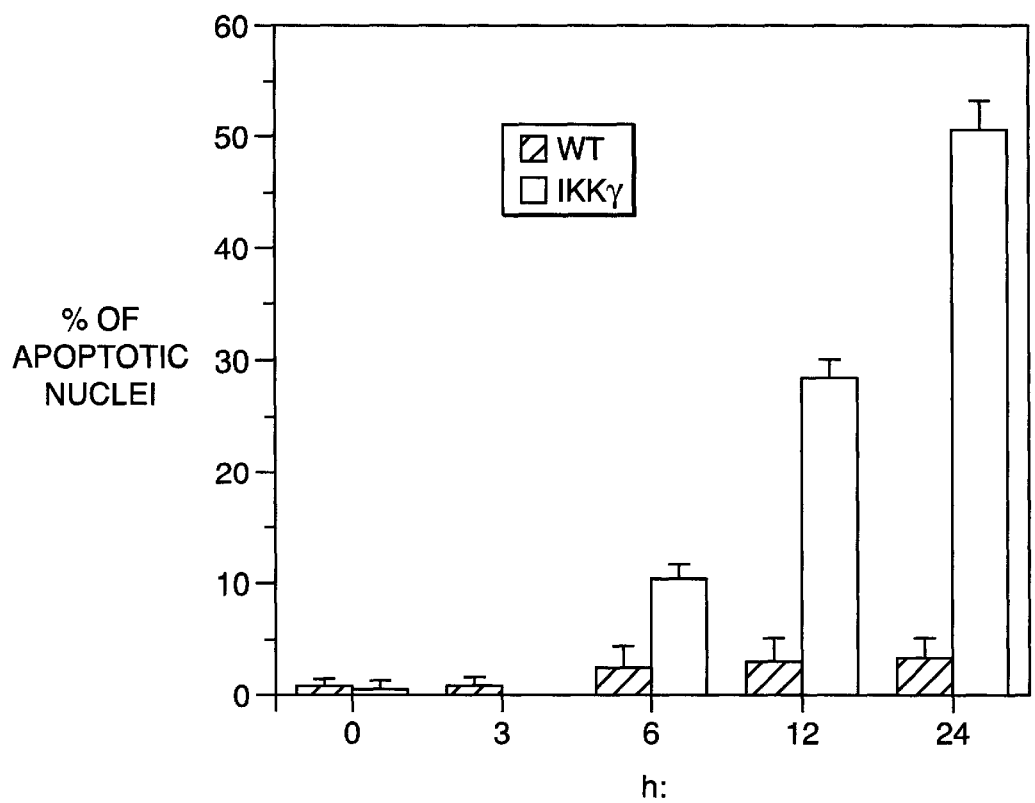

To facilitate understanding of the invention, a number of terms are defined and discussed below.

The term "gene" refers to a DNA sequence that comprises control and coding sequences necessary for the production of a polypeptide or its precursor. The polypeptide can be encoded by a full length coding sequence or by any portion of the coding sequence.

As used herein, the term "wild type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene.

In contrast, the terms "mutant" and "mutation" refer to a gene or gene product which displays modifications in sequence and or functional properties (i.e., altered characteristics) when compared to the wild-type gene or gene product. It is noted that naturally-occurring mutants can be isolated and these are identified by the fact that they have altered characteristics when compared to the wild-type gene or gene product.

The term "transgenic" refers to any organism into which at least one gene or gene fragment from another species has been introduced or in which an endogenous gene has been specifically inactivated. The term also describes any organism whose genome has been altered by in vitro manipulation of the early embryo or fertilized egg. The transgenic non-human animals of the invention include vertebrates such as rodents, non-human primates, ovines, bovines, ruminants, lagomorphs, porcines, caprines, equines, canines, felines, aves, etc. Murines (e.g., rats and mice), are the preferred nonhuman animal of the invention.

"Transgene" refers to a foreign gene inserted by artifice into a cell that becomes part of the genome of the cell, cell line, tissue or organism (i.e., either stably integrated or as a stable extrachromosomal element). The term "foreign gene" refers to any nucleic acid (e.g., gene sequence) which is introduced into the genome of an animal by experimental manipulations and may include gene sequences found in that animal so long as the introduced gene does not reside in the same location as does the naturally-ocurring gene.

The term "endogenous" refers to a gene or gene product that is native to the biological system, species or chromosome under study. An "endogenous" gene does not contain nucleic acid elements encoded by sources other than the chromosome on which it is normally found in nature. In contrast, the terms "exogenous" and "heterologous" refer to a gene or gene product that is foreign to the biological system, species or chromosome under study.

As used herein, the term "heterozygous" refers to genetic variation observed at a given gene locus (i.e., an organism with a diploid genotype has two different alleles of the gene of interest).

The term "pathology" refers to the anatomic and/or physiological deviations from the normal that constitute a disease. In the present invention, "incontinentia pigmenti pathology" refers to any symptoms associated with IP, including but not limited to blistering, hypopigmentation, hyperpigmentation, hair loss, abnormal teeth, visual problems and central nervous system abnormalities. At the cellular level, incontinentia pigmenti pathology also encompasses hypersensitivity to TNFα-induced apoptosis, dermatopathy, keratinocyte hyperproliferation and skin inflammation.

"Apoptosis" and/or "programmed cell death" refer to the genetically determined process of intracellular cell destruction. This process is distinct from the process of necrosis. Characteristics of apoptosis induced by TNFα, include but are not limited to DNA fragmentation and membrane blebbing.

"Dermatopathy" is a general term used in reference to skin disease. In the context of incontinentia pigmenti, "dermatopathy" typically refers to blistering lesions and the cellular destruction leading to hypopigmentation and hyperpigmentation.

"Keratinocyte hyperproliferation" refers to the overgrowth of keratin-producing epidermal cells.

"Hyperkeratosis" refers to the overgrowth of the skin keratin layer resulting in the production of skin with a rough or horny texture.

As used herein, the term "inflammation," refers to the process of capillary dilation and leukocytic infiltration leading to redness, heat, pain and swelling. In healthy individuals, inflammation serves as a mechanism to eliminate noxious agents or damaged tissue in the event of injury.

The term "candidate agent" refers to any molecule of any composition, including proteins, peptides, nucleic acids, lipids, carbohydrates, organic molecules, inorganic molecules, and/or combinations of molecules which are suspected to be capable of producing a physiological or biological response.

As used herein, the terms "reduction" and "decrease" refer to the act of inhibiting, diminishing, suppressing, alleviating, preventing or eliminating. In the broadest sense, the terms "reduction" and "decrease" encompass a range of effects from completely eliminating to partially inhibiting the process of interest.

"Biopsy material" refers to tissue, cells, or fluids removed from a living body for the purposes of examination. As used herein, the term "biopsy material" is not limited to any particular method used to obtain the material (e.g., needle, sponge, swab scapel, etc.).

The terms "immunoblot" and "Western blot" refer to methods of detecting a specific protein or proteins in a complex protein mixture such as a cell extract or lysate. These methods, which are well known in the art (See, e.g., Towbin et al, *Proc Natl Acad Sci USA* 76:4350–4354 [1979]; and Ausubel et al. (eds.), *Current Protocols in Molecular Biology*, John Wiley & Sons, Inc., New York [1994]), involve fractionating the protein mixture by SDS-polyacrylamide gel electrophoresis, transferring the separated proteins onto a solid support such as nitrocellulose and detecting the protein(s) of interest by with an antibody. The bound primary antibody can be visualized by the use of a secondary antibody conjugated to an enzyme which produces a signal in the presence of a suitable substrate.

As used herein, the term "Northern blot" refers to methods for transferring denatured RNA onto a solid support for use in a subsequent hybridization assay. Total RNA or polyA-enriched RNA is typically electrophoresed in an agarose gel, transfered to a membrane and probed with a radioactively-labeled DNA or RNA fragment to detect specific RNA sequences. Northern blots are routinely used in the art (See, e.g., Thomas, *Proc Natl Acad Sci USA* 77:5201–5205 [1980]; and Ausubel et al. (eds.), *Current Protocols in Molecular Biology*, John Wiley & Sons, Inc., New York [1994]).

The term "Southern blot," as used herein, refers to methods for transferring denatured DNA, which has been fractionated by agarose gel electrophoresis, onto a solid support, for use in a subsequent hybridization assay. These methods typically entail the digestion of genomic DNA with a suitable restriction enzyme prior to agarose gel electrophoresis, transfer of the DNA to a membrane and incubation with a radioactively-labeled DNA or RNA fragment for detection of specific DNA sequences. Southern blots are routinely used in the art (See, Southern, *J. Mol Biol* 98:503–517 [1975]; and Ausubel et al., supra [1994]).

As used herein, the term "polymerase chain reaction (PCR)" refers to a method for increasing the concentration of a segment of a target sequence in a DNA mixture without cloning or purification (See, e.g., U.S. Pat. Nos. 4,683,195, 4,683,202, and 4,965,188, hereby incorporated by reference). This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." When the template is RNA, a reverse transcription (RT) step is completed prior to the amplification cycles. Thus, this variation and the method is termed "RT-PCR."

The terms "single-strand conformation polymorphism" and "SSCP," as used herein, refer to the ability of single strands of nucleic acid to take on characteristic conformations under non-denaturing conditions, which in turn can influence the electrophoretic mobility of the single-stranded nucleic acids. Changes in the sequence of a given fragment (i.e., mutations) will also change the conformation, consequently altering the mobility and allowing this to be used as an assay for sequence variations (Orita et al., *Genomics* 5:874–879 [1989]).

As used herein, the terms "conformation-sensitive gel electrophoresis" or "CSGE" refer to methods for detecting mutations which involve distinguishing DNA heteroduplexes from homoduplexes via mildly denaturing gel electrophoresis. CSGE protocols are well known in the art (Ganguly et al., *Proc Natl Acad Sci USA* 90:10325–10329 [1993]).

DESCRIPTION OF THE INVENTION

The present invention relates to compositions and methods involving IKKγ mutants. In particular, the present invention provides methods and compositions, including transgenic animals, suitable for use in determining means to treat, control, and/or prevent incontinentia pigmenti (IP). The present also provides methods to detect the presence of mutations in the IKKγ gene and protein.

In view of the marked similarity in symptoms, inheritance and chromosomal location between human IP and the Ikkγ/NEMO mutations in the mouse, experiments were conducted during the development of the present invention to examine the expression of IKK subunits in skin biopsies and fibroblasts from IP patients. While biopsies from normal individuals were found to be invariably and uniformly positive for expression of all IKK subunits, biopsies taken from affected areas of IP patients were positive for IKKα and IKKβ, but expression of IKKγ/NEMO was strikingly reduced. Fibroblasts taken from a male fetus and a newborn, whose mother was diagnosed with IP, were found to be completely deficient in expression of IKKγ/NEMO. Thus, it is believed that human IP is caused by defective IKKγ/NEMO expression. In both mouse and human female carriers, pathogenesis is contemplated as being dependent upon sequential hyperproliferation and apoptosis of IKKγ/NEMO-deficient cells that are generated through X-chromosome inactivation (Lyonization). However, an understanding of the mechanism(s) is not necessary in order to make and use the present invention.

The IKK Complex

The IKK complex is composed of the IKKα and IKKβ catalytic subunits (DiDonato et al., *Nature* 388:548–554 [1997]; Mercurio et al., *Science* 278:860–866 [1997]; Régnier et al., *Cell* 90:373–383 [1997]; and Zandi et al., *Cell* 91:243–252 [1997]), and the IKKγ/NEMO regulatory subunit (Rothwarf et al., *Nature* 395:297–300 [1998]; and Yamaoko et al., *Cell* 93:1231–1240 [1998]). This complex is essential for activation of NF-κB transcription factors (Rothwarf and Karin, *Science's STKE* [1999]). NF-κB activation by proinflammatory stimuli is required for induction of genes whose products are involved in both innate and adaptive immunity (Ghosh et al., *Ann. Rev. Immunol.* 16:225–260 [1998]). NF-κB target genes include chemokines, cytokines, adhesion molecules and enzymes that produce secondary inflammatory mediators. In addition, NF-κB activation is required for protection of cells from apoptosis, especially that caused by members of the tumor necrosis factor (TNF) family of death cytokines (Beg and Baltimore, *Science* 274:782–784 [1996]; Liu et al., *Cell* 87:565–576 [1996]; Van Antwerp et al., *Science* 274:787–789 [1996]; and Wang et al., *Science* 274:784–787 [1996]). Purified recombinant IKKα and IKKβ both phosphorylate the IκB inhibitors of NF-κB, at sites that cause their ubiquitin-mediated degradation in vivo (Zandi et al., *Science* 281:1360–1363 [1998]). However, IKKα:IKKβ dimers that form in the absence of IKKγ/NEMO, and even those that associate with C-terminally truncated IKKγ/NEMO, are refractory to most NF-κB activators, including interleukin 1 (IL-1), double-stranded (ds) RNA, bacterial lipopolysaccharide (LPS), and TNFα (Rothwarf et al., supra [1998]; and Yamaoka et al., supra [1998]). As a result, IKKγ/NEMO-deficient cells are practically devoid of NF-κB activity, even after cell stimulation (Yamaoka et al, supra [1998]).

Genetic analysis of IKK function through gene targeting in mice revealed that despite the high degree of sequence similarity and identical substrate specificity, the two catalytic subunits of the IKK complex dramatically differ in their biological functions. IKKα is required for proper development and differentiation of the epidermis and other ectodermal derivatives, but is not required for IKK activation by proinflammatory stimuli (Hu et al., *Science* 284:316–320 [1999]; and Takeda et al., *Science* 284:313–316 [1999]), nor for induction of NF-κB activity in the affected cell types. Therefore, it is unlikely that IKKα function in control of keratinocyte differentiation is exerted via NF-κB. In contrast, IKKβ is essential for IKK and NF-κB activation by proinflammatory stimuli. Ikkb$^{-/-}$ mice die at mid-gestation due to massive liver apoptosis and IKKβ-deficient cells are sensitive to TNFα-induced apoptosis (Li et al., *Proc. Natl. Acad. Sci. USA* 96:1042–1047 [1999], Li et al., *Genes Dev.* 13:1322–1328 [1999]; and Tanaka et al. *Immunity* 10:421–429 [1999]). This phenotype is essentially identical to that of RelA$^{-/-}$ mice which lack the p65 subunit of NF-κB (Beg et al., *Nature* 376:167–169 [1995]). However, an understanding of the mechanism(s) is not necessary in order to make and use the present invention.

IKKγ/NEMO Genotypes and Phenotypes

Unlike the genes coding for the catalytic subunits of the IKK complex, the IKKγ/NEMO gene, which codes for the essential IKKγ/NEMO regulatory subunit is located on the X-chromosome. Due to this chromosomal location and random X chromosome inactivation (Lyonization), loss-of-function Ikkγ/NEMO mutations result in different phenotypes in female and male mice. While mutant males die in utero, as expected for a complete IKK and NF-κB deficiency (Li et al., *Proc. Natl. Acad. Sci. USA* 96:1042–1047 [1999], Li et al., *Genes Dev.* 13:1322–1328 [1999]; and Tanaka et al. *Immunity* 10:421–429 [1999]), heterozygous mutant females are born alive, but display a severe, yet transient, multi-organ disease. The cutaneous signs of the disease detected in Ikkγ$^{+/-}$ female mice are very similar to those observed in human patients suffering from IP. Both␣kkγ$^{+/-}$ mice and female IP patients eventually recover, reach sexual maturity, and can transmit the disease to the next generation. Like Ikkγ/NEMO mutant mice and cells, cells and tissues from IP patients exhibit defective IKKγ/NEMO expression.

The two Ikkγ/NEMO loss-of-function mutations that were generated during the development of the present invention, resulted in a complete loss of IKKγ/NEMO expression and are therefore null mutations. Given the importance of IKKγ/NEMO for IKK and NF-κB activation (Rothwarf et al., supra [1998]; and Yamaoka et al., supra [1998]), it was expected that Ikkγ/NEMO mutant males would die at mid-gestation from severe liver degeneration, caused by massive apoptosis. The severity of this phenotype (also reported by Rudolph et al., *Genes Dev.* 14:854–862 [2000]), appears to be directly proportional to the severity of the NF-κB deficiency, with IKKγ/NEMO-deficient cells and mice exhibiting almost undetectable levels of basal and inducible NF-κB DNA-binding activity. However, an understanding of the mechanism(s) is not necessary in order to make and use the present invention.

Although both IKKγ/NEMO and IKKα deficiencies result in epidermal abnormalities, the characteristic signs are distinct, and apart from hyperproliferation of basal keratinocytes, bear little resemblance to each other. Most importantly, terminal differentiation markers are overexpressed in the Ikkγ$^{+/-}$ epidermis, but are not expressed in the Ikkγ$^{-/-}$ epidermis (Hu et al., *Science* 284:316–320 [1999]; and Tanaka et al., *Immunity* 10:421–429 [1999]). Also, no inflammation was detected in IKKα-deficient mice, which die shortly after birth. These results strongly suggest that IKKγ/NEMO is not required for the epidermal function of IKKα, which is probably not mediated via NF-κB, whose activation is highly dependent upon IKKγ/NEMO. However, an understanding of the mechanism(s) is not necessary in order to make and use the present invention.

IKKγ/NEMO Physiological Functions and Involvement in IKKα and IKKβ-Specific Functions During the development of the present invention, the physiological functions of the IKKγ/NEMO subunit and its involvement in the IKKα- and IKKβ-specific functions were investigated. In these experiments, mice carrying two different targeted disruptions of the IKKγ/NEMO locus were produced. Both the human (Jin and Jeang, *J. Biomed. Sci.* 6:115–120 [1999]) and mouse IKKγ/NEMO loci are closely linked to G6PD, an X-linked locus, which has been mapped to Xq28 in humans (Chen et al., *Hum. Mol. Genet.* 5:659–668 [1996]). Consistent with the X chromosomal location and the importance of IKKγ/NEMO for NF-κB activation, IKKγ/NEMO mutant male embryos die at about embryonic day (E) 12, exhibiting essentially the same phenotype as IKKβ-deficient mice (i.e., massive liver apoptosis). The phenotype of Ikkγ$^{+/-}$ female mice was surprising. Indeed, it was observed that female mice heterozygous for either of the IKKγ/NEMO mutations exhibited a severe, but self-limiting dermopathy (genodermatosis) and transient growth retardation. Thus, as indicated above, characteristics of the compound disorder and its pattern of inheritance are strikingly similar to those associated with the human X-linked genodermatosis incontinentia pigmenti (IP).

Although a recent report (Rudolph et al, supra [2000]) stated that Ikkγ$^{+/-}$ females are normal and viable, all of the Ikkγ$^{+/-}$ females obtained from targeted ES cells during the development of the present invention exhibited severe disease shortly after birth. Some of the chimeric mice exhibited a similar disease, especially when the ES cell contribution to their skin was extensive. The basis of the difference between the results described herein and those of Rudolph et al. are not clear, but it is contemplated that they are related to the use of different ES cells (R1 versus E14).

Figure 3A:
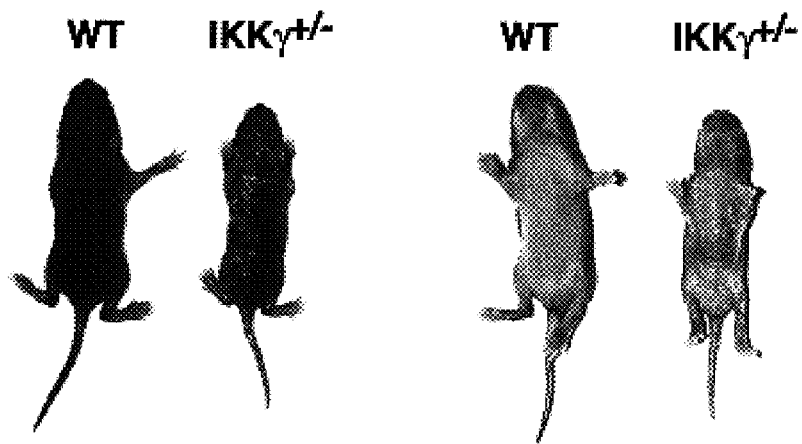
FIGS. 3A–3B illustrates severe dermatopathy in Ikkγ$^{+/-}$ female mice. Panel A provides photographs of dorsal views (left) and ventral views (right) of day 6 wild-type and Ikkγ$^{+/-}$ littermate females. Panel B provides skin sections showing the cutaneous phenotype of wild-type and Ikkγ$^{+/-}$ littermate females. These photographs of day 2 mice include both low (top panel) and high (bottom panel) magnification views of dorsal skin. Arrows indicate spots of increased pigmentation in IKKγ$^{+/-}$ skin. The photographs indicated as "Day 6" provide views of dorsal and hind skin (top panels), ventral skin (middle panels), and heads (bottom panels). The photographs indicated as "Day 10," show striped fur (second panel) and hyperkeratotic lesion (bottom panel) in an Ikkγ$^{+/-}$ mouse as compared to a wild-type littermate (top panel).
Figure 3B:
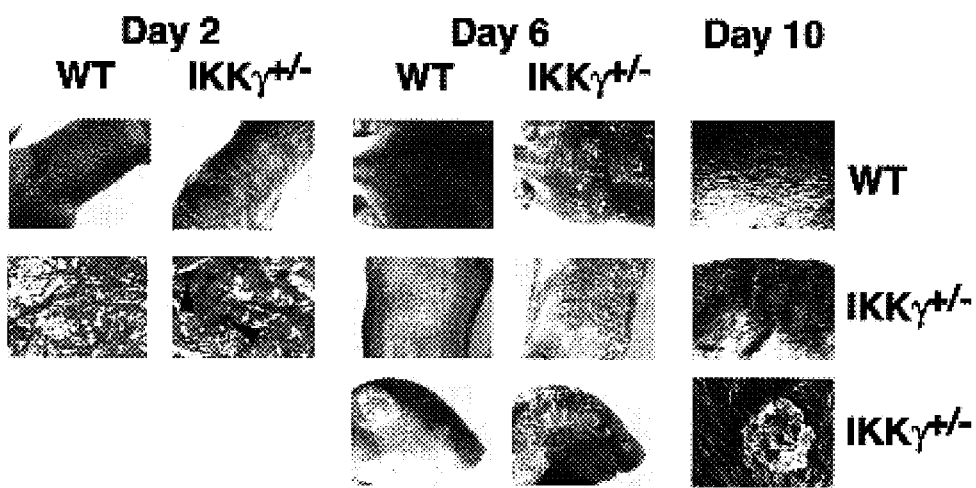
Figure 4A:
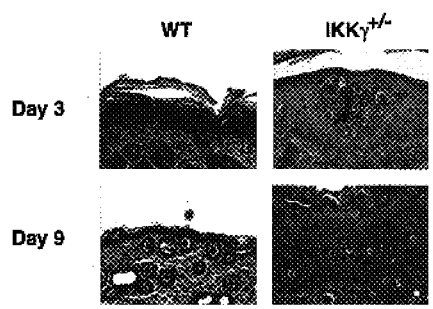
FIGS. 4A–4D shows histopathology of wild-type and Ikkγ$^{+/-}$ skin. Panel A shows 400× H&E-stained sections of back skin from day 3 and day 9 wild-type and Ikkγ$^{+/-}$ female mice. The arrow points to an intraepidermal microvesicle containing numerous granulocytes (day 3). Panel B provides electron micrographs (2600×) of lead acetate-stained, back skin sections from day 9 female wild-type and Ikkγ$^{+/-}$ mice. Panel C provides fluorescent immunohistochemistry photographs (400×) of skin sections stained with specific antibodies to cytokeratin 5 (cK5), cK6, cK17, and filaggrin, to show the expression of differentiation, proliferation and inflammation markers in skin of day 3 and day 9 wild-type and Ikkγ$^{+/-}$ female mice. Panel D provides fluorescent photomicrographs (400×) showing expression of IKKγ/NEMO in back skin of day 9 wild-type and Ikkγ$^{+/-}$ mice. In these photographs, blue dots are nuclei and pink stain corresponds to IKKγ/NEMO.
Figure 4B:
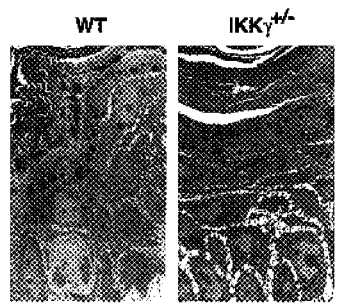
Figure 4C:
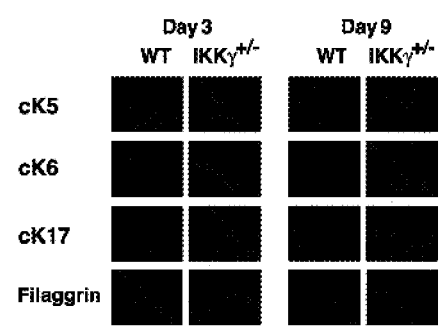
Figure 4D:

Newborn Ikkγ$^{+/-}$ females were indistinguishable from wild-type littermates. However, these Ikkγ$^{+/-}$ female mice exhibited a severe dermatopathy shortly after birth. Initially, the disease presents mostly as severe inflammation, with very red and blistery skin and overall failure to thrive. By day 2, these animals exhibited a patchy pigmentation that progressed to severe inflammation accompanied by hyperkeratotic lesions, as shown in FIG. 3, Panel A. Closer examination revealed spotty melanin deposits in certain areas of the Ikkγ$^{+/-}$ skin, as shown in the bottom panel of FIG. 3, Panel B.

After day 5, the Ikkγ$^{+/-}$ females were about half the size and weight as their wild-type littermates (See, FIG. 3, Panel A). Furthermore, Ikkγ$^{+/-}$ females showed generalized erythematous eruption of the skin and sparse hair growth, as shown in FIG. 3, Panels A and B. This was followed by development of hyperkeratotic lesions, which were shed by day 8 or 9 (See, FIG. 3, Panel A). By day 8, many of the Ikkγ$^{+/-}$ females were frequently found on their backsides or immobile on their sides. These animals also exhibited spasms, tremors, and locomotor difficulties. By day 9, approximately 55% of the Ikkγ$^{+/-}$ females had died, having a severely runted and anemic appearance. Tail sections taken from day 8 or 9 Ikkγ$^{+/-}$ mice showed severe diffuse hyperplasia of the epidermis, with multifocal hyperkeratosis and parakeratosis, as well as infiltration of neutrophils in both the epidermis and dermis. The bone marrow in the tail consisted of blood-filled spaces with no hematopoietic cells.

By day 10, surviving Ikkγ$^{+/-}$ females (around 45%) showed striped fur and a few focal hyperkeratotic lesions, as shown in FIG. 3, Panel B. After one month, the remaining verrucous growths dropped off, giving rise to bald areas (alopecia). By this time, most of the surviving females had recovered, gained weight, and were almost indistinguishable from wild-type littermates. The surviving Ikkγ$^{+/-}$ females are fertile and transmit the disease to their progeny.

Chemokines and Cytokines Associated with IP and Disease in Ikkγ$^{+/-}$ Mice

In both Ikkγ$^{+/-}$ mice and IP patients, the first stage of the disease is inflammatory, with massive granulocyte infiltration into the epidermis (Machado-Pinto, *Semin. Cutan. Med. Surg.* 15:308–316 [1996]). The biochemical basis for increased migration of granulocytes in IP patients remains unknown. However, increased production of chemokines, detected in the skin of Ikkγ$^{+/-}$ mice (e.g., RANTES and MIP-2), is likely to account for the inflammatory infiltrate. As most, if not all, of the cytokine genes whose expression is elevated in the Ikkγ$^-$ skin are thought to be under NF-κB control (Barnes and Karin, *New Engl. J. Med.* 336:1066–1071 [1997]), they are likely to originate from Ikkγ$^+$ cells, because Ikkγ$^-$ cells are devoid of NF-κB activity. Most likely, some of the abnormally hyperproliferating Ikkγ$^-$ keratinocytes undergo necrosis and their released cell contents elicit an inflammatory response in adjacent Ikkγ$^+$ cells. The signalling mechanism underlying this response remains to be identified. Regardless, an understanding of this mechanism(s) is not necessary in order to use the present invention. Nonetheless, it has been recently shown that heat shock proteins can activate Toll-like receptors and induce cytokine production (Asea et al., *Nat. Med.* 6:435–442 [2000]; and Ohashi et al., *J. Immunol.* 164:558–561 [2000]). However, it is well-established that inhibition of NF-κB activity results in hyperproliferation of both human and mouse keratinocytes, but does not prevent their terminal differentiation (Seitz et al., *Proc. Natl. Acad. Sci. USA* 95:2307–2312 [1998]). Hyperproliferation coupled with normal keratinocyte differentiation gives rise to the hyperkeratotic lesions, seen in both Ikkγ$^{+/-}$ mice and IP patients.

Like most other NF-κB-deficient cells, the IKKγ/NEMO-deficient keratinocytes are very sensitive to apoptosis; TUNEL assays revealed a large increase in the frequency of apoptotic cells in the epidermis of Ikkγ$^{+/-}$ mice. Increased apoptosis was not limited to the epidermis, but was also seen in the thymus and spleen. In all of these cases, apoptosis may be enhanced or driven by death cytokines produced by neighboring IKKγ/NEMO-positive cells. Many of the TUNEL-positive cells in the epidermis of Ikkγ$^{+/-}$ mice were clustered and appeared to be extruded from the epidermis by growth of the remaining normal cells. Most likely, this process contributes to the shedding of dead skin fragments and the eventual disappearance of the verrucous lesions. The third stage of the disease is characterized by streaks of hyperpigmentation and scarring (Landy and Donnai, *J. Med. Genet.* 30:53–59 [1993]; and Francis and Sybert, *Semin. Cutan. Med. Surg.* 16:54–60 [1997]). Histological examination reveals loss (incontinence) of melanin from basal cells of the epidermis and the appearance of free pigment deposits, or melanin-containing macrophages (Francis and Sybert, supra [1997]; and Scheuerle, *J. Med. Genet.* 77:201–218 [1998]). Although an understanding of the mechanism(s) is not necessary in order to use the present invention, the loss of pigment cells appears to be due to the apoptosis and necrosis of IKKγ/NEMO-deficient cells that release free melanin, some of which is ingested by macrophages. Eventually, all or most of the IKKγ/NEMO-deficient cells are eliminated through apoptosis and wherever possible, are replaced by surviving and proliferation-competent IKKγ/NEMO-expressing cells (See, FIG. 8). However, it is believed that some residual IKKγ/NEMO-deficient cells are capable of giving rise to another disease cycle, as has been occasionally observed (van Leeuwen et al., *Pediatr. Dermatol.* 17:70 [2000]). The importance of the IKK complex and NF-κB for prevention of apoptosis in humans, as well as mice is underscored by the contemplated association between human IP and IKKγ/NEMO-deficiency.

Figure 8:
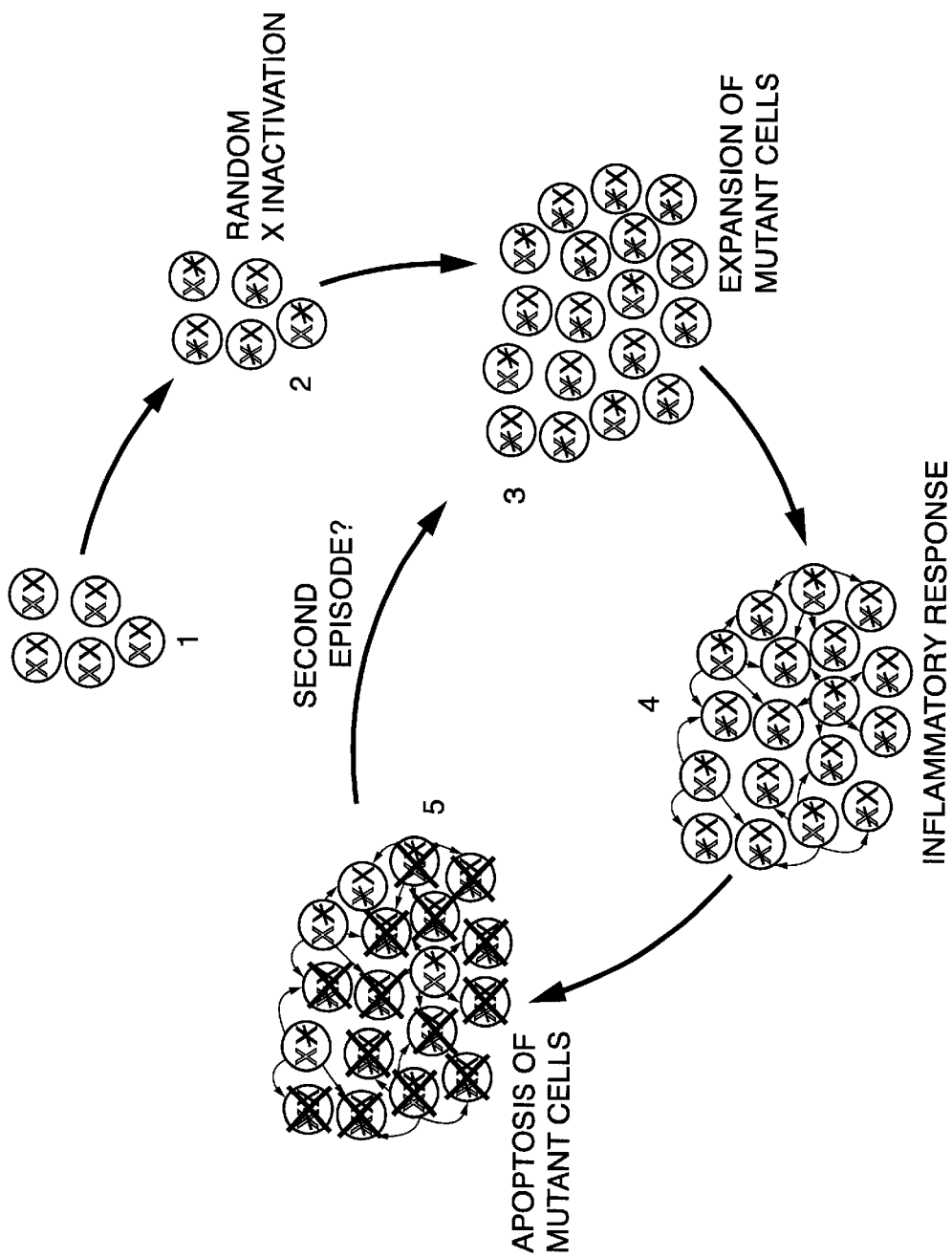
FIG. 8 provides a schematic of a contemplated pathway proposed to lead to the dermatopathy observed in Ikkγ$^{+/-}$ mice and human IP patients.

Thus, although and understanding of the mechanism is not necessary in order to use the present invention, the observations made during the development of the present invention provide clarification of the pathogenesis associated with IP. FIG. 8 provides a schematic of the progression of this pathology. In this Figure, step 1 indicates that both the wild-type (white) and mutant (black) X chromosomes are active. Step 2 indicates that some cells express either the wild-type or mutant X-chromosome, through random X-inactivation (e.g., in basal cells of the epidermis). Step 3 indicates that due to the absence of NF-κB activity, which negatively regulates keratinocyte proliferation, the cells that express the mutant X expand, while in step 4, these cells elicit an inflammatory response in the adjacent cells that expressed the wild-type X chromosome. It is contemplated that this reaction is triggered by necrosis of some of the mutant cells. In step 5, death cytokines produced by wild-type cells kill the IKKγ/NEMO-deficient cells. If a few IKKγ/NEMO-deficient basal or stem cells survive, a second episode of hyperproliferation, followed by inflammation and cell death can be initiated.

IKKγ/NEMO Deficiency Mouse Model for Incontinentia Pigmenti

Whereas heterozygosity for autosomal null mutations can result in up to 50% reduction in gene expression, X-linked null mutations through random X inactivation (Lyonization) give rise to mosaics composed of cells that either express or do not express the gene product. The pattern of inheritance and expression, the sequential cutaneous alterations, and the male lethality associated with Ikkγ/NEMO mutations in mice are similar to those described for the human genodermatosis IP (Francis and Sybert, supra [1997]; and Scheuerle, supra [1998]). Furthermore, the IP gene (Sefiani et al., Genomics 4:427–429 [1989]; and Sefiani et al., Hum. Genet. 86:297–299 [1991]) and the human IKKγ/NEMO locus (Jin and Jeang, supra [1999]) are both located at Xq28. Indeed, biopsies from affected skin of IP patients (11 out of 11) showed normal expression of IKKα and IKKβ, but spotty and diminished expression of IKKγ/NEMO in comparison to skin from normal individuals or patients suffering from other skin diseases (e.g., psoriasis or X-linked ichthyosis). While residual IKKγ/NEMO expression in IP females is probably due to the presence of normal (presumably Ikkγ$^+$) cells, human fibroblast cultures established from a male fetus and a male newborn whose mother and grandmother were diagnosed with IP, were completely deficient in IKKγ/NEMO expression. In neither case was IKKα nor IKKβ expression altered. These and other results strongly suggest that the human genodermatosis, IP, is also caused by mutations at or near the IKKγ/NEMO locus, which at least in one family, completely prevented IKKγ/NEMO expression. Preliminary results indicated the absence of detectable IKKγ/NEMO mRNA in the male IP-derived fibroblasts, as well as a large deletion encompassing the 5' end of the IKKγ/NEMO gene.

The similarities between the Ikkγ/NEMO mutant mice and human IP patients are quite extensive. In both cases, the initial stage of the disease is inflammatory, and histological analysis reveals massive infiltration of granulocytes into the epidermis. In both affected mice and humans, the inflammatory stage is followed by hyperkeratotic lesions that are eventually shed, and in both cases, hyperproliferation of epidermal keratinocytes occurs. In both cases, the typical altered pigmentation, from which the name of the human disease is derived, is detected in streaks that follow Blaschko's lines (which are thought to reflect the process of X-chromosome inactivation) or their equivalents in mice. Most importantly, in most of the human cases and in a large proportion (45%) of the mutant mice, these cutaneous manifestations are transient and the affected females reach sexual maturity and are fertile.

Additional symptoms exhibited by Ikkγ$^{+/-}$ mice and human IP patients are remarkably similar. For example, 30% of IP patients exhibit certain neurological manifestations (Carney, Arch. Dermatol. 112:535–542 [1976]). Although it is difficult to compare human and mouse behavior, quite a few of the Ikkγ$^{+/-}$ mice exhibit tremors and locomotor difficulties, indicative of neurological defects. In addition, although no immunological deficiencies have been described for IP patients, the Ikkγ$^{+/-}$ mice exhibited dramatically increased apoptosis in both their thymii and spleens. Although an understanding of the mechanism(s) is not necessary in order to use the present invention, it is not known whether these lymphoid organ alterations lead to permanent immune deficiencies in adult Ikkγ$^{+/-}$ mice.

Thus, in view of the striking similarities in disease presentation and progression, the Ikkγ mutant mouse strains established during the development of the present invention, provide useful animal models for human IP.

Experimental

The following examples are provided in order to demonstrate and further illustrate certain preferred embodiments and aspects of the present invention and are not to be construed as limiting the scope thereof.

As used herein, the following abbreviations apply: wt (wild-type); ° C. (degrees Centigrade); rpm (revolutions per minute); FBS (fetal bovine serum); H$_2$O (water); HCl (hydrochloric acid); aa (amino acid); bp (base pair); kb (kilobase pair); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); MgCl$_2$ (magnesium chloride); NaCl (sodium chloride); PAGE (polyacrylamide gel electrophoresis); PBS (phosphate buffered saline [150 mM NaCl, 10 mM sodium phosphate buffer, pH 7.2]); PCR (polymerase chain reaction); SDS (sodium dodecyl sulfate); Tris (tris(hydroxymethyl)aminomethane); w/v (weight to volume); v/v (volume to volume); Imgenex (Imgenex, San Diego, Calif.); ATCC (American Type Culture Collection, Rockville, Md.); Sigma (Sigma Chemical Co., St. Louis, Mo.); Santa Cruz (Santa Cruz Biologicals, Santa Cruz, Calif.); Stratagene (Stratagene Cloning Systems, La Jolla, Calif.); Pharmingen (BD Pharmingen, San Diego, Calif.); Torrey Pines Biolabs (Torrey Pines Biolabs, San Diego, Calif.); Clontech (Clontech, Palo Alto, Calif.); Baxter (Baxter Healthcare, Deerfield, Ill.); NEN (NEN/Lifescience, Boston, Mass.); Difco (Difco Laboratories, Detroit, Mich.); Life Technologies (Life Technologies, Inc., Gaithersburg, Md.); and Covance (Covance Research Products, Inc., Denver, Pa.).

EXAMPLE 1

Generation of IKKγ/NEMO Deficient Mice

In these experiments, Ikkγ/NEMO deficient mice were produced. First, the Ikkγ/NEMO gene was cloned from a mouse genomic library. Its first exon was found to be located 3 kb away from the first exon of the X-linked G6PD gene in a head-to-head arrangement. Such close linkage was also found for the human genes (Jin and Jeang, supra [1999]). Therefore, human IKKγ/NEMO is located at Xq28 and positioned next to G6PD (Chen et al., Hum. Mol. Genet. 5:659–668 [1996]).

Then, seven independent phage clones containing the murine Ikkγ/NEMO locus were isolated by screening a 129/SvJ mouse genomic library (Stratagene). A 6 kb fragment containing exons 1 and 2 of the Ikkγ/NEMO gene was subcloned into the CWKO targeting vector (Westphal and Leder, Curr. Biol. 7:530–533 [1997]), using methods known in the art.

To disrupt the mouse Ikkγ/NEMO locus, two targeting vectors (shown in FIG. 1) were generated. The first vector inserts a β-lactamase (BLA1) expression cassette in-frame with the first ten (10) codons of Ikkγ/NEMO. The BLA1 cassette contains a stop codon and is followed by a Neor cassette. The second vector has most of the coding region of the first exon removed and replaced by the BLA1 and Neor cassettes.

A total of 25 μg of linearized vector DNA was electroporated into 10$^7$ male-derived mouse R1 ES cells, as known in the art (See e.g., Nagy et al., Proc. Natl. Acad. Sci. USA 90:8424–8428 [1993]). After positive-negative selection using 150 μ/ml G418 and 0.2 μM FIAU, G418-resistant colonies were picked, screened by PCR, and confirmed by Southern blot analysis using BglII-digested genomic DNA and an external probe shown in FIG. 1, Panel A. Homologous integration of either vector resulted in cells that no longer expressed the IKKγ/NEMO polypeptides that were detected in wild-type (wt) cells (See, FIG. 1B).

Two clones of IKKγ⁻ ES cells corresponding to each targeting vector (for a total of 4 different ES clones) were injected into C57BL/6J blastocysts to generate chimeras. All of the clones gave rise to germ-line chimeras. Male chimeras were crossed with C57BL/6J females, resulting in germline transmission. Two different chimeric mice derived from each targeting vector were used to generate Ikkγ$^{+/-}$ females that transmitted the mutations to their progeny. The phenotypes caused by either mutant allele were identical. Therefore, in the following experiments, the two mutations are not distinguished. Some of the chimeric mice suffered from a transient skin disease, but eventually recovered, as discussed in greater detail below.

Heterozygous females were confirmed by PCR analysis of tail DNA with the primers P1 (5'-TCCGGTTCTGTCGGAGCGGTC-3'; SEQ ID NO:1) and P2 (5'-ACCCACTCGTGCACCCAACTG-3'; SEQ ID NO:2). Sex determination was done using the following primers: SRY1 (5'-GAGAGCATGGAGGGCCAT-3'; SEQ ID NO:3); SRY2 (5'-CCACTCCTCTGTGACACT-3'; SEQ ID NO:4); ZFY1 (5'-GACTAGACATGTCTTAACATCTGTCC-3'; SEQ ID NO:5); and ZFY2 (5'-CCTATTGCATGGACTGCAGCTTATG-3'; SEQ ID NO:6). The SRY primers gave rise to an approximately 200 bp PCR product in male embryos only, and an approximately 120 bp PCR product was detected in both male and female embryos with the ZFY primers.

EXAMPLE 2

Cell Culture and Mouse Embryonic Fibroblasts (MEFs)

In this Example, the cell cultures used in the development of the present invention are described. Primary human embryonic fibroblasts W138 and HEL229 (both obtained from ATCC) were maintained in Dulbecco's modified Eagle's medium (DMEM), containing 10% FBS, L-glutamine (2 mM; Life Technologies), penicillin (1000 units/ml)/streptomycin (1000 μg/ml) (i.e., Pen/Strep). Primary human fibroblasts from an aborted male fetus and a male IP newborn (Roberts et al. [1998]) were grown in RPMI 1640 supplemented with 10% FBS, L-glutamine and Pen/Strep. Primary MEFs were derived from E12 Ikkγ⁻ or wild-type fetuses and grown in DMEM supplemented with 10% FBS, L-glutamine, and Pen/Strep.

To measure cytotoxicity, MEFs were plated on LabTek tissue culture slides and treated with 50 ng/ml TNFα. Controls (i.e., without TNFα treatment) were also used. At the times indicated in FIG. 1, Panel E, cells were fixed in 4% paraformaldehyde in PBS for 30 minutes at room temperature, permeabilized with 0.1% Triton X-100 in PBS for 10 minutes, and stained with DAPI (1:3000 in PBS; Sigma) for 5 minutes at room temperature, and mounted with a coverslip. Slides were viewed using an epifluorescence-equipped microscope. Apoptotic nuclei were scored by counting at least 100 cells in five random fields for each experimental condition. Each experiment was conducted in duplicate, using at least two different MEF preparations. The values shown in FIG. 1 are percentages of apoptotic nuclei scored using a fluorescent microscope. Commensurate with the defect in NF-κB activation, Ikkγ⁻ MEFs were extremely sensitive to TNFα-induced apoptosis (See, FIG. 1, Panel E).

EXAMPLE 3

Immunoprecipitation, Kinase, Immunoblot and Electrophoretic Mobility Shift Assays In these experiments, MEFs and ES cell extracts were examined. Wild-type and Ikkγ mutant MEFs and ES cells were treated with TNFα (10 ng/ml) or IL-1 (20 ng/ml). Control cells (i.e., without TNFα or IL-1 treatment) were also included. At the times indicated in FIG. 1, Panel C, the IKK complex was immunoprecipitated from cell lysates with a polyclonal antibody directed against IKKα (M280, Santa Cruz), and its activity measured by an immunocomplex kinase assay with GST-1κBα (1-54) as a substrate, as known in the art (See, Rothwarf et al., Nature 395:297–300 [1998]). Loading was normalized by immunoblotting with a monoclonal antibody against IKKα (1:500; Imgenex). Immunoblot analysis was conducted as known in the art and previously described (See, Hu et al., Science 284:316–320 [1999]). Electrophoretic mobility shift assays (EMSA) were performed as known in the art (See, Rothwarf et al., supra [1998]).

Consistent with the absence of IKKγNEMO, no IKK activity could be elicited in Ikkγ⁻ ES cells or murine embryo fibroblasts (MEFs) stimulated with TNFα or IL-1 (See, FIG. 1, Panel C). Furthermore, no NF-κB DNA-binding activity could be induced in IKKγ/NEMO-deficient cells, and even basal NF-κB activity was dramatically reduced (See, FIG. 1, Panel D). Expression of the p50 and p65 subunits of NF-κB, however, was normal in IKKγ/NEMO-deficient MEFs. In addition, IKKα and IKKβ expression was found to be unaltered in all of the IKKγ/NEMO-deficient ES clones (the genotype of these cells is referred to herein as "Ikkγ⁻," regardless of origin).

EXAMPLE 4

RNA Preparation and RNase Protection Assay

Figure 5A:
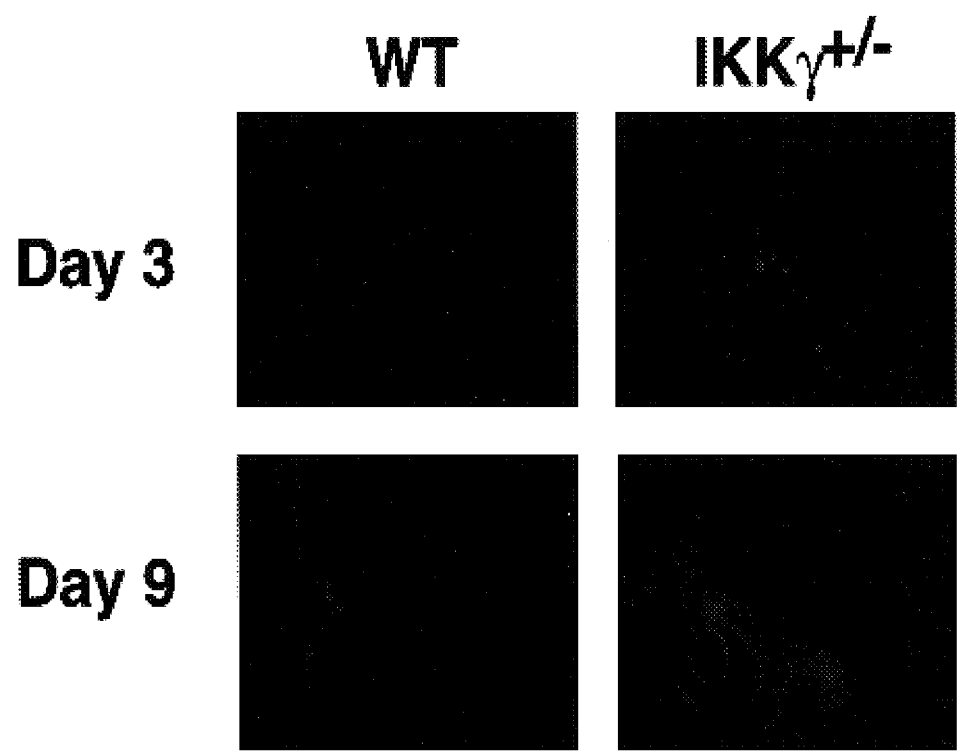
FIGS. 5A–5C shows increased proliferation, apoptosis, and chemokine gene expression in Ikkγ$^{+/-}$ skin. Panel A shows skin sections from day 3 and day 6 wild-type and Ikkγ$^{+/-}$ mice pulsed with bromodeoxyuridine (BrdU) for 2 hours. The skin sections were fixed and paraffin-embedded, and then stained with anti-BrdU antibody and visualized by fluorescent immunohistochemistry. Panel B shows paraffin sections of day 3 wild-type and Ikkγ$^{+/-}$ back skin analyzed by TUNEL staining. Panel C shows expression of chemokine mRNA.
Figure 5B:
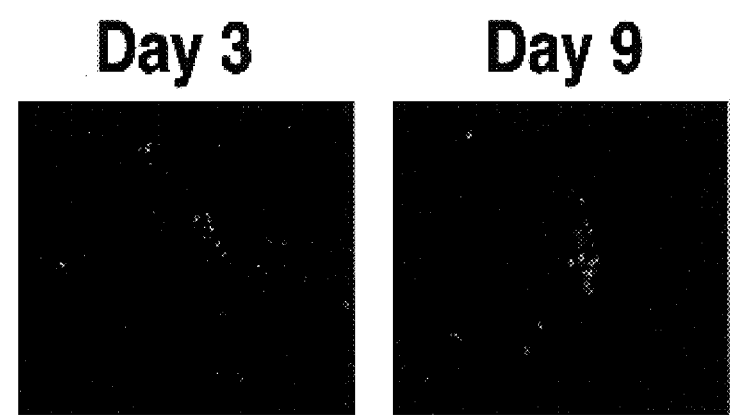
Figure 5C:
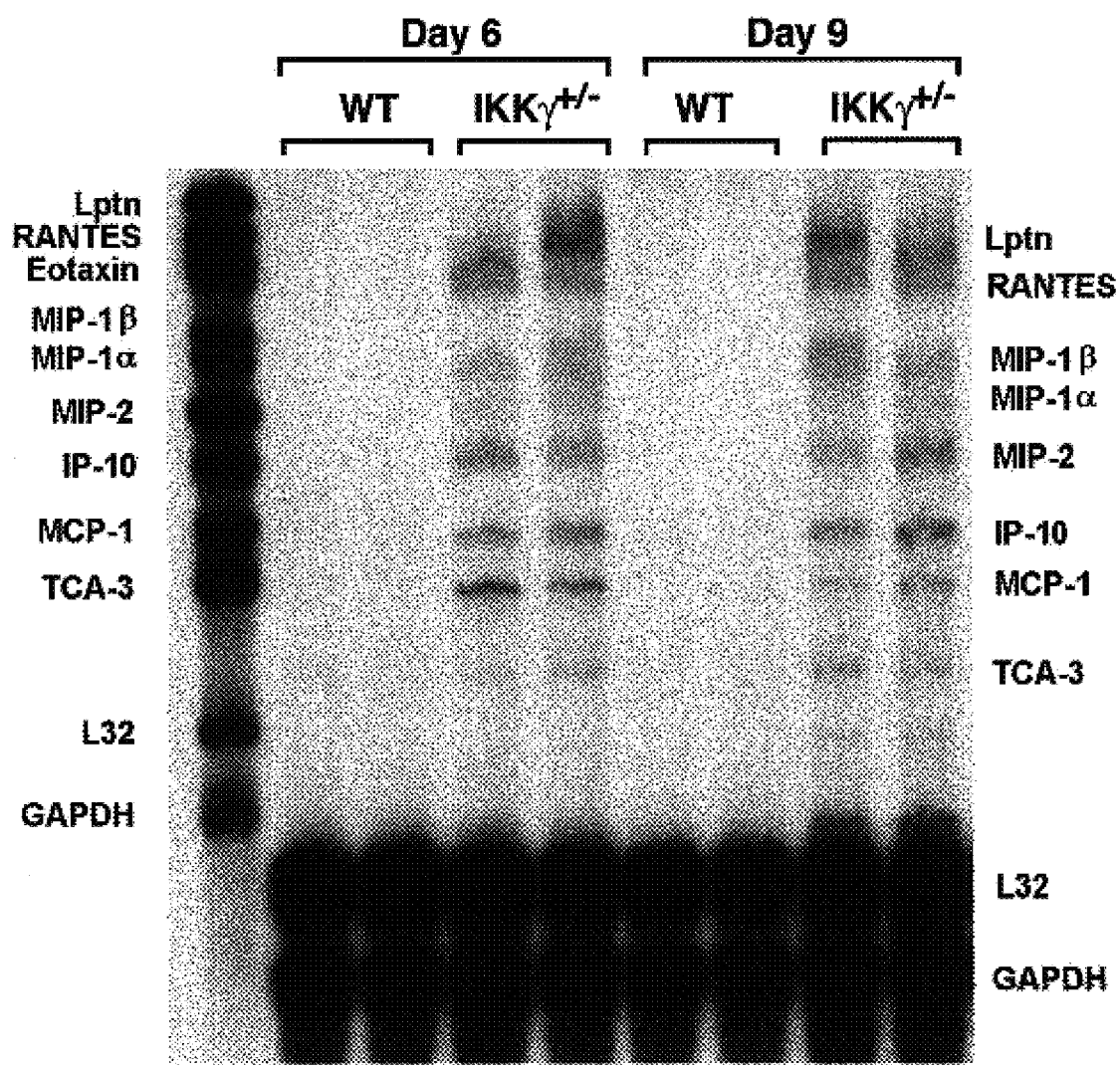

In this Example, the RNA assays used in the development of the present invention are described. Total RNA was prepared using TRIzol reagent (Life Technologies), following the manufacturer's instructions. Briefly, 4 μg samples of total RNA from wild-type and Ikkγ$^{+/-}$ day 6 and day 9 skin were hybridized with [α$^{32}$P] UTP-labeled riboprobes transcribed from mCK2 and mCK5 template sets. RNAse protection assays were carried out using the RPA kit (Torrey Pines Biolabs), as known in the art (See e.g., Feng et al., Am. J. Physiol. 266:713–722 [1994]). Riboprobes were generated from RiboQuant mCK2 and mCK5 multiprobe template sets (Pharmingen). The gels were dried and exposed overnight. FIG. 5, Panel C provides a gel showing results from these experiments. In this gel, the protected bands are shorter than the probe because the polylinker regions present in the probe are not protected.

RNAse protection analysis of total RNA isolated from day 6 and day 9 wild-type and Ikkγ$^{+/-}$ skin, revealed a dramatic increase in expression of numerous chemokine genes, including RANTES, MIP-1α, MIP-1β, MIP-2, IP-10, MCP-1, lymphotactin, and TCA-3, in the mutant skin. Elevated expression of several cytokine mRNAs in Ikkγ$^{+/-}$ skin were also observed, including IL-1α, IL-1β, TNFα, IFN-γ, TGFβ1, and TGFβ2. Interestingly, most of these genes are believed to be NF-κB targets (Barnes and Karin, New Engl. J. Med. 336:1066–1071 [1997]).

EXAMPLE 5

Histology, In Situ TUNEL Assay and Transmission Electron Microscopy

In this Example, various methods to observe histopathology associated with the phenotype of IKKγ/NEMO-deficient mice were investigated. The animals tested in these experiments were the results of crossing Ikkγ$^{30}$ /− females with C57BL/6J males. No live Ikkγ$^-$ males were identified among the progeny of these crosses. As IKKβ and RelA/p65 deficiencies result in lethality around E13 to E15, due to massive liver apoptosis (Beg et al., supra [1995]; Li et al., supra [1999]; and Tanaka et al, supra [1999]), the progeny of timed pregnancies at E12 were examined. The genotype and sex of each fetus were determined by PCR-based assays. All of the Ikkγ$^-$ males were dead at E12, while all of the Ikkγ$^+$ males were alive and had normal morphology. While most of the Ikkγ$^{+/-}$ female fetuses were alive and indistinguishable from Ikkγ$^{+/+}$ females, dead Ikkγ$^{+/-}$ females were occasionally observed.

Mouse embryo (E12) livers and organs of neonate mice were fixed in 10% buffered formalin and embedded in paraffin or frozen directly following their removal in OCT compound (Baxter). Tissue sections (5 μm thick) were stained with hematoxylin and eosin (H&E) for histological analysis. In situ TUNEL assays were performed using the ApoAlert DNA fragmentation assay kit (Clontech) according the the manufacturer's instructions. Electron microscopy on back skin sections of day 9 mice was performed as known in the art (See e.g., Hu et al, supra [1999]).

Figure 2A:
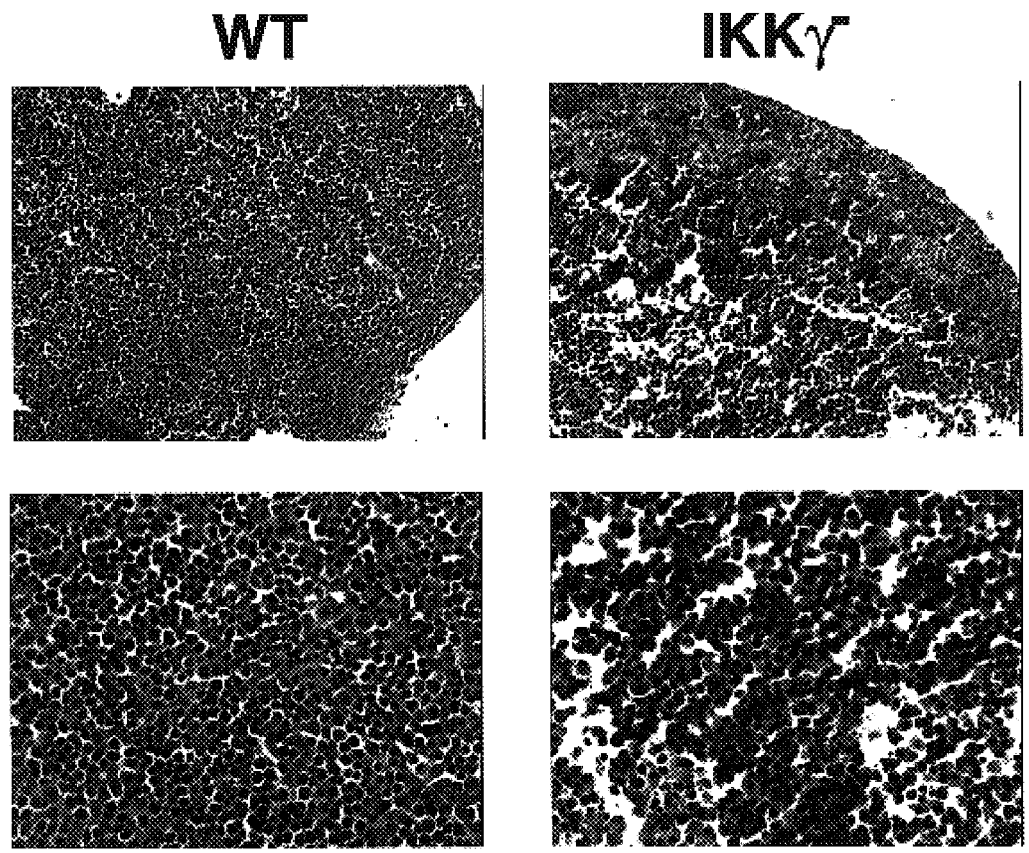
FIGS. 2A–2B illustrates the severe liver apoptosis observed in Ikkγ$^-$ male embryos. Panel A provides photomicrographs of livers from wild-type and Ikkγ$^-$ E12 male fetuses which were fixed in 10% formalin and paraffin embedded. Transverse sections were stained with hematoxylin and eosin (H&E). In the top panes, the magnification is 200×; in the bottom panes, the magnification is 400×. Panel B provides photomicrographs of terminal deoxynucleotidyl transferase dUTP nick end labeling (TUNEL) staining of sectioned livers from E12 embryos (400×).
Figure 2B:
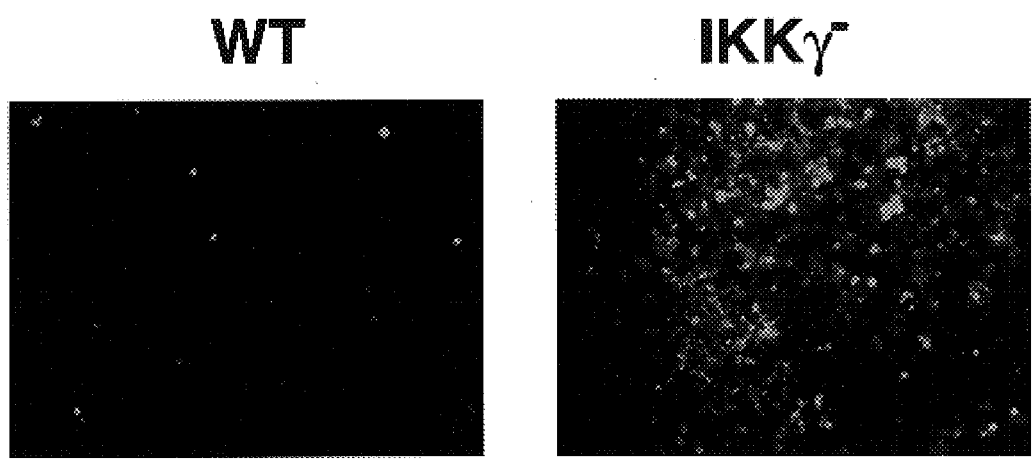

Histochemical examination revealed that the livers of Ikkγ$^-$ males were largely devoid of normal-appearing hepatocytes and contained large hemorrhagic areas, as shown in FIG. 2, Panel A. TUNEL assays indicated a massive increase in the number of apoptotic cells in Ikkγ$^-$ livers in comparison with Ikkγ$^+$ livers, as shown in FIG. 2, Panel B. The livers of some Ikkγ$^{+/-}$ female embryos also contained high numbers of apoptotic cells, but were not as severely degenerated and hemorrhagic as the livers of Ikkγ$^-$ males. These results are entirely consistent with the severe NF-κB deficiency and sensitivity to TNFα-induced apoptosis associated with IKKγ/NEMO deficiency (See, FIG. 1).

Histopathology of day 9 livers revealed abundant extramedullary hematopoiesis (EMH) in both the sinusoids and around the portal triads of Ikkγ$^{+/-}$ tissues. The hematopoietic cells were mostly granulocytes with variable numbers of megakaryocytes. In wild-type livers, only a slight amount of EMH confined to the sinusoids was observed.

In addition to the liver abnormalities described above, thymus and spleen tissue sections indicated that day 9 Ikkγ$^{+/-}$ females had extremely small thymii and spleens. Histological examination revealed massive diffuse destruction of cortical lymphocytes. The cortex was composed of bare stromal cells sprinkled with nuclear debris (See, FIG. 6, Panel A). The medulla at the corticomedullary junction was primarily composed of large epithelioid cells, with abundant pale cytoplasm and large nuclei that appeared to be dendritic cells. The more central portion of the medulla contained medium-sized lymphocytes and scattered dendritic cells stuffed with nuclear debris. TUNEL assay indicated that the destruction of cortical lymphocytes in the Ikkγ$^{+/-}$ thymus resulted from increased apoptosis (See, FIG. 6 Panel B).

Figure 6A:
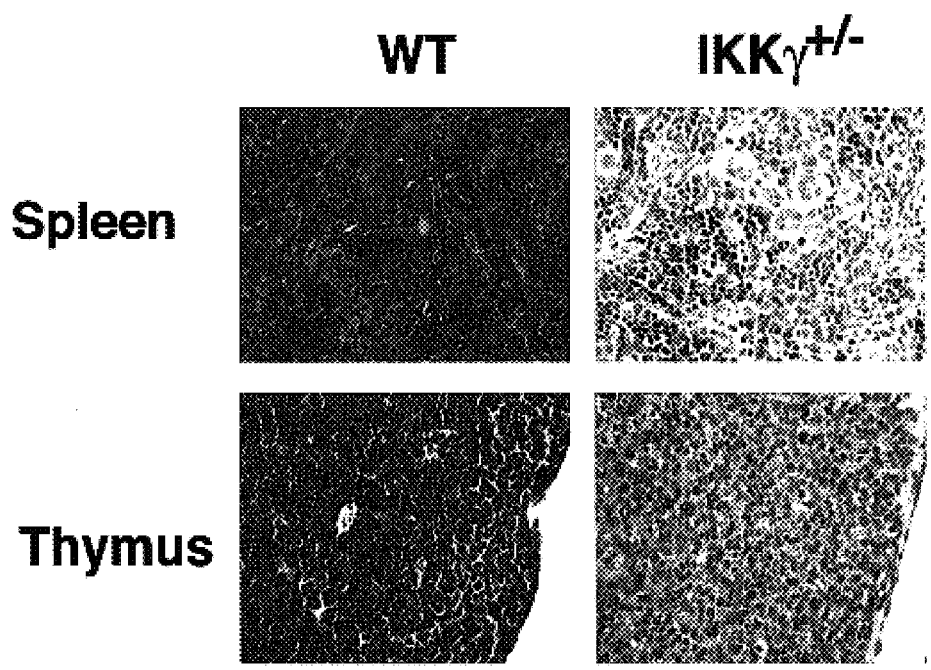
FIGS. 6A–6B illustrates splenic and thymic abnormalities in Ikkγ$^{+/-}$ mice. Panel A shows sections from day 9 IKKγ$^{+/-}$ and wild-type female littermates, stained with H&E (400×), while Panel B shows sections subjected to TUNEL staining (400×).
Figure 6B:
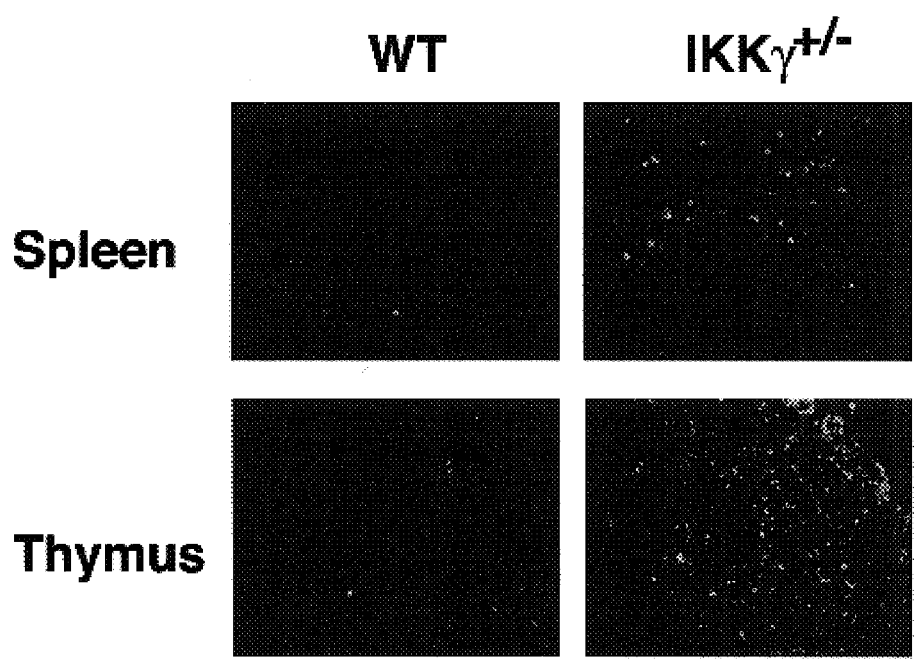

Histological examination of day 9 Ikkγ$^{+/-}$ spleens revealed that the white pulp was barely discernable and lacked a marginal zone (FIG. 6, Panel A). At day 6, the white pulp was composed of stromal support cells with a few macrophages containing nuclear debris. Megakaryocytes were readily discernable in the red pulp, but there were a few clusters of erythroid cells and no groupings of granulocytes. TUNEL assays of Ikkγ$^{+/-}$ spleen sections showed a marked increase in the number of apoptotic cells in comparison to wild-type spleen sections (See, FIG. 6, Panel B).

Sections of the sternum revealed that the growth plates on the the sternebrae were normal in day 9 Ikkγ+/− mice Thus, it is unlikely that the smaller size of Ikkγ$^{+/-}$ females was due to a skeletal growth defect. The bone marrow within the sternum was moderately cellular and composed almost entirely of nearly mature granulocytes with segmented nuclei. No megakaryocytes were found. The bone marrow of wild-type littermates was densely cellular and contained numerous megakaryocytes. Granulocytes with segmented nuclei represented only 10%–15% of the wild-type bone marrow cells. Furthermore, between 60% and 69% of the bone marrow cells isolated from day 6 and day 9 Ikkγ$^{+/-}$ femurs were myeloid and polymorphic nuclear cells in comparison to only 26%–31% in age-matched wild-type bone marrow.

EXAMPLE 6

In Vivo BrdU Incorporation

In this Example, in vivo labelling with bromodeoxyuridine (BrdU) was used to confirm that the thickness of the Ikkγ$^{+/-}$ epidermis and elevated expression of basal cytokeratins were due to hyperproliferation of keratinocytes (See, FIG. 5, Panel A). Mice were injected intraperitoneally with BrdU (100 μg/g; Sigma) and killed after 2 hours. Skin sections were processed as known in the art (See e.g., Hu et al., supra [1999]). Paraffin embedded sections were stained with anti-BrdU (1:100; Sigma) and visualized by fluorescent immunohistochemistry using tyramide signal amplification (TSA) kits (NEN/Life Science).

TUNEL staining revealed dispersed apoptotic keratinocytes in day 3 Ikkγ$^{+/-}$ epidermis, and by day 9, large clusters of apoptotic cells were detected, as shown in FIG. 5, Panel B. No apoptotic cells were detected in age-matched wild-type control skin.

EXAMPLE 7

Dermal Immunohistochemistry

In this Example, experiments used during the development of the present invention to observe dermatopathology are described. Transverse sections of mouse skin (5 μm thick) were deparaffinized with xylene and rehydrated through graded ethanol. Sections were stained as known in the art and described by Hu et al. (Hu et al., supra [1999]) with anti-cK1, anti-cK5, anti-cK6, anti-cK10, anti-cK14, anti-cK17, anti-filaggrin, anti-involucin, and anti-loricin. All antisera were used at 1:5000 dilution and were obtained from Covance, with the exception of anti-cK17, which was obtained from P.A. Coulombe. Frozen skin sections were stained with purified anti-IKKγ (3294; 1:2000). All slides were visualized by fluorescent immunohistochemistry with TSA kit (NEN/Life Science).

Human skin samples (4 μm thick) were deparaffinized and rehydrated as above, prior to staining with anti-IKKα (H744), anti-IKKβ (H470), or anti-IKKγ (L17). All of these antibodies were obtained from Santa Cruz, and were diluted 1:80. The chromogen reaction, resulting in a visible brown precipitate was developed using the ImmunoCruz (Santa Cruz) staining system according to the manufacturer's recommendations.

Mouse Experiments

In these experiments, histological sections of wild-type and Ikkγ$^{+/-}$ female skin were observed. Sections obtained from newborn animals revealed normal epidermis and no morphological differences. However, by day 3, the Ikkγ$^{+/-}$ epidermis was diffusely hyperplastic, containing 6–8 layers versus the normal 3–4 layers as shown in FIG. 4, Panel A. The Ikkγ$^{+/-}$ epidermis also contained large microvesicles full of numerous eosinophils and neutrophils. Cells in the basal layers were mildly elongated and disorganized. At day 9, the Ikkγ$^{+/-}$ epidermis was even more hyperplastic and was composed of 8–12 cell layers (See, FIG. 4, Panel A). The outer 3–5 cell layers contained prominent keratohyaline granules (See, FIG. 4, Panels A and B). The stratum corneum was thickened, with keratin arranged in compacted sheets (lamellar hyperkeratosis). Scattered throughout the Ikkγ$^{+/-}$ epidermis were degenerate keratinocytes characterized by shrunken, deeply eosinophilic cytoplasm, and pyknotic nuclei. Multifocal areas of mild intercellular edema were found in the epidermis of day 9 Ikkγ$^{+/-}$ animals. These areas were absent in wild-type tissue. The Ikkγ$^{+/-}$ dermis was hypercellular due to infiltrates of neutrophils, with a lesser number of mast cells and occasional eosinophils. Although day 9 Ikkγ$^{+/-}$ skin was found to have a thicker epidermis, overall, it was much thinner (2–3 times) than wild-type skin, due to the lack of subcutaneous fat. Cells with pyknotic nuclei were also found in the root sheaths within Ikkγ$^{+/-}$ skin. Electron microscopy revealed that the Ikkγ$^{+/-}$ keratinocytes were separated by intercellular edema (spongiosis), as shown in FIG. 4, Panel B.

The expression levels of several differentiation, proliferation, and inflammation markers were also examined. No differences were observed between newborn Ikkγ$^{+/-}$ females and wild-type littermates. However, at day 3, there was a marked increase in expression of basal cytokeratins (cK) 5 and 14, and hyperproliferative cytokeratins (cK6 and cK17) in Ikkγ$^{+/-}$ epidermis, as compared to wild-type tissue, as shown in FIG. 4, Panel C. It has been established that expression of cK6 and cK17 in the epidermis results from an inflammatory response (Ma et al., *Gene Expr.* 6:361–370 [1997]). Intriguingly, no changes in expression of the suprabasal cytokeratins cK1 and cK10, nor an increase in terminal differentiation markers (filaggrin [FIG. 4, Panel C], involucrin and loricin) were detected. However, at day 9, increased expression of all basal and suprabasal cytokeratins and terminal differentiation markers in the Ikkγ$^{+/-}$ epidermis was observed, as shown in FIG. 4, Panel C. Whereas in wild-type day 9 skin, IKKγ/NEMO was uniformly expressed in the epidermis and to a lesser extent in hair follicles, IKKγ/NEMO staining was patchy in the Ikkγ$^{+/-}$ epidermis, as shown in FIG. 4, Panel D. Although an understanding of the mechanism in not necessary in order to use the present invention, it is contemplated that this heterogeneity is due to random X inactivation (Lyonization), resulting in clones of IKKγ/NEMO-positive and -negative cells. Importantly, at day 9, the number of IKKγ/NEMO-negative cells was found to be considerably higher than the number of IKKγ/NEMO-positive cells.

Human IP Fibroblasts and Skin Biopsy Samples

Figure 7A:
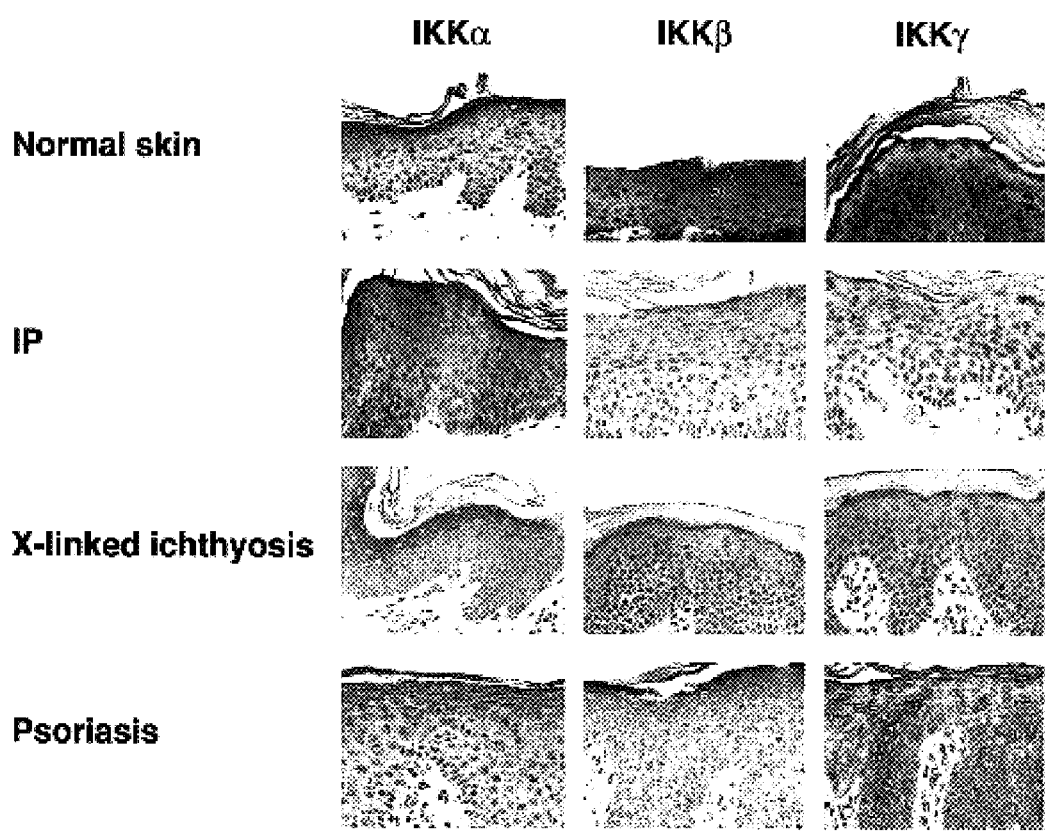
FIGS. 7A–7B shows the expression of IKK subunits in human skin biopsies and fibroblasts. Panel A shows (400×) sections from normal individuals and IP patients, individuals with X-linked ichthyosis, and individuals with psoriasis. These sections were stained using specific antibodies against IKKα, IKKβ, or IKKγ/NEMO. The immune complexes were visualized by chromogen reaction, resulting in a brown precipitate. Sections were counterstained with hematoxylin. Panel B shows IKKγ/NEMO expression in human fibroblasts. In this Panel, lane 1 contains HEL229, lane 2 contains W138, lane 3 contains a fibroblast sample from IP patient 1, and lane 4 contains a fibroblast sample from IP patient 2.
Figure 7B:
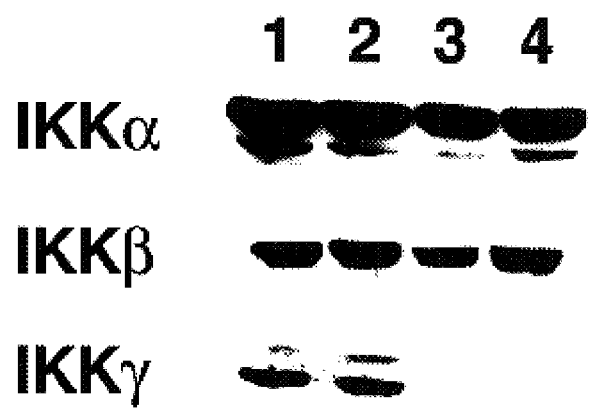

These experiments were conducted in view of the similarity in the skin manifestations observed in Ikkγ$^{+/-}$ female mice and those associated with IP, as well as the identical chromosomal location of the IKKγ/NEMO and IP loci in humans. Thus, the level of IKK subunit expression was investigated using human skin biopsy materials. Immunohistochemical analysis revealed uniform expression of all three IKK subunits in epidermis of normal individuals as well as patients suffering from X-linked ichthyosis and psoriasis, as shown in FIG. 7, Panel A. IKKα and IKKβ were also invariantly and uniformly expressed in the epidermis of 11 different IP patients. However, scarce and sporadic expression of IKKγ/NEMO in a few cells within the epidermis was found in biopsies taken from lesions of 11 different IP patients (See, FIG. 7, Panel A, for data from one representative biopsy). Western blot analysis of two primary fibroblast cultures, established from an aborted male fetus, as well as a newborn which died within one day of birth (both of which were carried by the same IP mother), showed no expression if IKKγ/NEMO, but normal expression of IKKα and IKKβ, as shown in FIG. 7, Panel B. Genomic linkage analysis confirmed that these fibroblasts contained the affected X chromosome (Roberts et al, *Am. J. Med. Genet.* 75:159–163 [1998]). Northern blot analysis revealed the absence of the IKKγ/NEMO gene product. Interestingly, the deceased IP newborn was found to have internal hemorrhage, excessive EMH, and granulocytic infiltrate in the lung, despite the absence of any identifiable infection (Roberts et al., supra [1998]).

EXAMPLE 8

Ocular Immunohistochemistry

Figure 9:
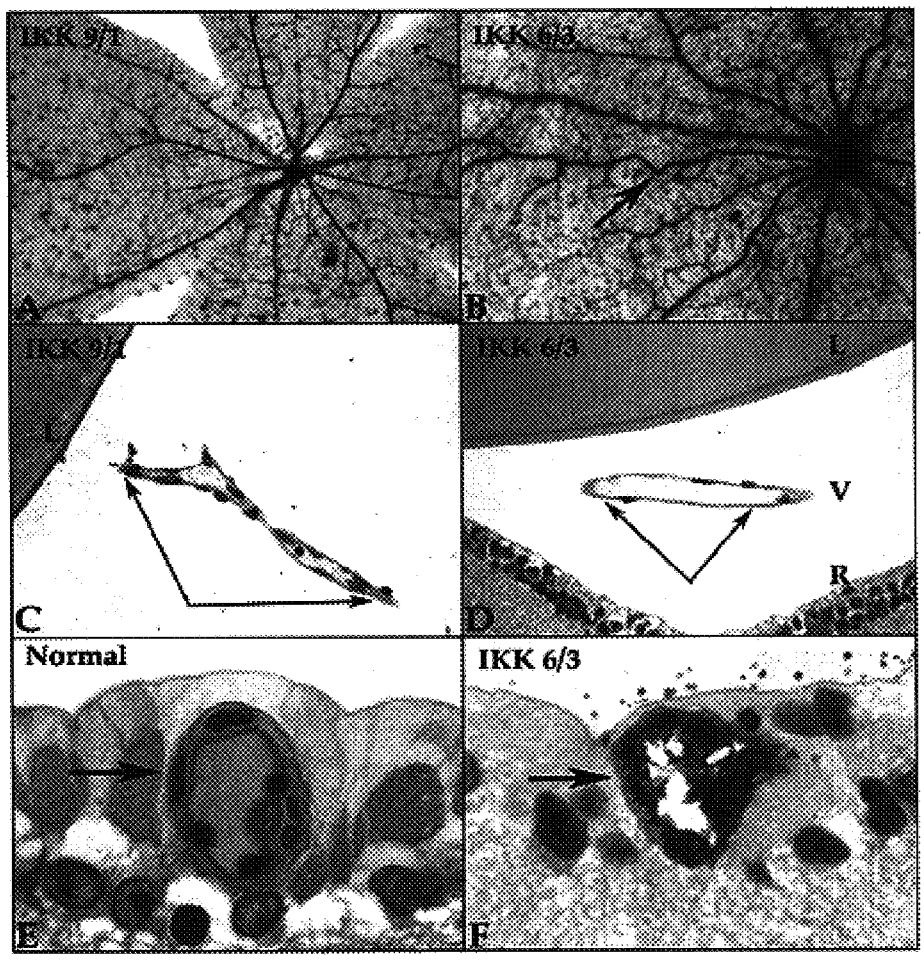
FIG. 9 shows abnormal ocular manifestations observed in IKKγ$^{+/-}$ mice. Panels A and B show ADPase-incubated, flat embedded retinas. Panel A shows the normal spoke wheel pattern, while Panel B shows the tortuous vessel pattern seen in some IKKγ$^{+/-}$ mice. Panels C and D show the persistent fetal vasculature observed in retinas of IKKγ$^{+/-}$ mice. The tortuous vessels seen in panel B have hyperplastic and hypertrophic endothelial cells and smooth muscle cells as indicated in Panel F. There was also duplication of the basement membrane in these blood vessels as indicated by comparison of a normal artery (Panel E) to an artery from a IKKγ+/− mouse (Panel F).

In this Example, experiments used during the development of the present invention to observe ocular pathology are described. Two significant histopathological changes in the eyes of Ikkγ$^{+/-}$ female mice were observed. First, in three Ikkγ$^{+/-}$ mice, at 17 days of age, a persistent hyaloid vasculature was seen. This vasculature should have regressed by 7 days of age. In particular, both the vasa hyaloidea propria and tunica vasculosa lentis were observed to be intact and the vasculature appeared viable (i.e., had viable cellular components and red blood cells in the lumens). Part of the persistent hyaloid system in vitreous is shown in FIG. 9, Panel C ( L indicates the lens). A few persistent and viable hyaloidal vessels were also found in an additional Ikkγ$^{+/-}$ mouse from another litter (FIG. 9, Panel D, R indicates retina). This persistence of the fetal vasculatures has been reported previously in human incontinentia pigmenti (See, Fard and Goldberg, *Arch. Ophthalmol* 116:682–684 [1998]).

The second major change was observed in ADPase-incubated, flat embedded retinas. Although there appeared to be a loss in viable retinal vessels (indicated by a loss of ADPase activity) early in the disease process, once these retinas were embedded, sectioned and analyzed, it was apparent that there were numerous viable vessels (i.e., endothelial cells, smooth muscle cells, and pericytes were all present). The vessel pattern observed on one animal is representative of the normal spoke wheel pattern (FIG. 9, Panel A). With age, however, the pattern became abnormal (FIG. 9, Panel B). Most notable was the tortuousity in arteries and veins typical of that observed in patients with hypertension. When these retinas were sectioned, the tortuous vessels had hyperplastic and hypertrophic endothelial cells and smooth muscle cells. There was also a duplication of the basement membrane in these blood vessels. This can best be observed by comparing a normal artery (arrow in FIG. 9, Panel E), with an artery from an Ikkγ$^{+/-}$ mouse (FIG. 9, Panel F). In some arteries, the duplication of basement membrane material was so extensive that the lumenal space was almost closed. This tortuousity and basement membrane reduplication was seen in six of six littermates at 3 months of age. Thus, there appear to be significant vascular changes in Ikkγ+/− mice. Accumulation of leukocytic infiltration was not generally observed, except in the vitreous area near the optic nerve head in a single Ikkγ+/− mouse. Complete vessel closure, as has been described in humans, was not found in any of the mice analyzed. However, the narrowing of the lumens may eventually result in complete closure with age.

EXAMPLE 9

Dental Morphology

Figure 10:
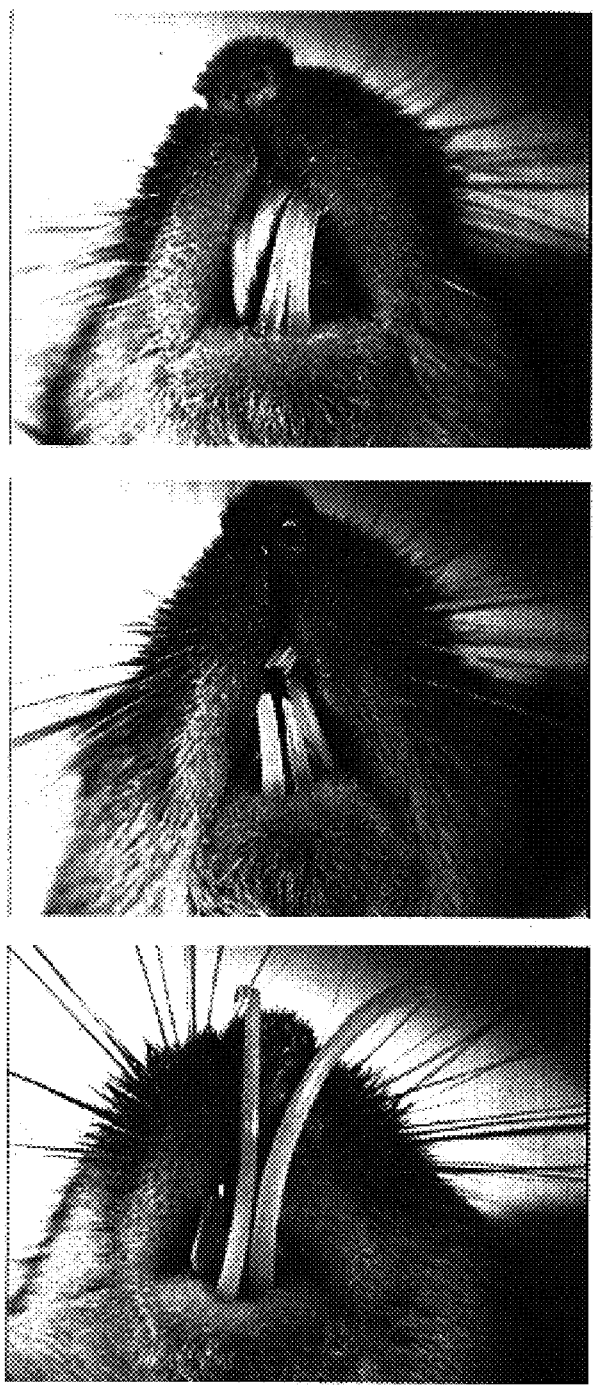
FIG. 10 shows the gross tooth abnormalities observed in some IKKγ+/− mice.

In this Example, the teeth of viable Ikkγ+/− mice are described. Upon examining the teeth of Ikkγ+/− mice, it appeared that approximately 10–15% of the transgenic Ikkγ+/− mice exhibited profound dental abnormalities (FIG. 10). These gross abnormalities are similar to those sometimes observed in human IP patients.

EXAMPLE 10

Amplification of the Ikkγ Exons in Human IP Patients

Figure 11A:
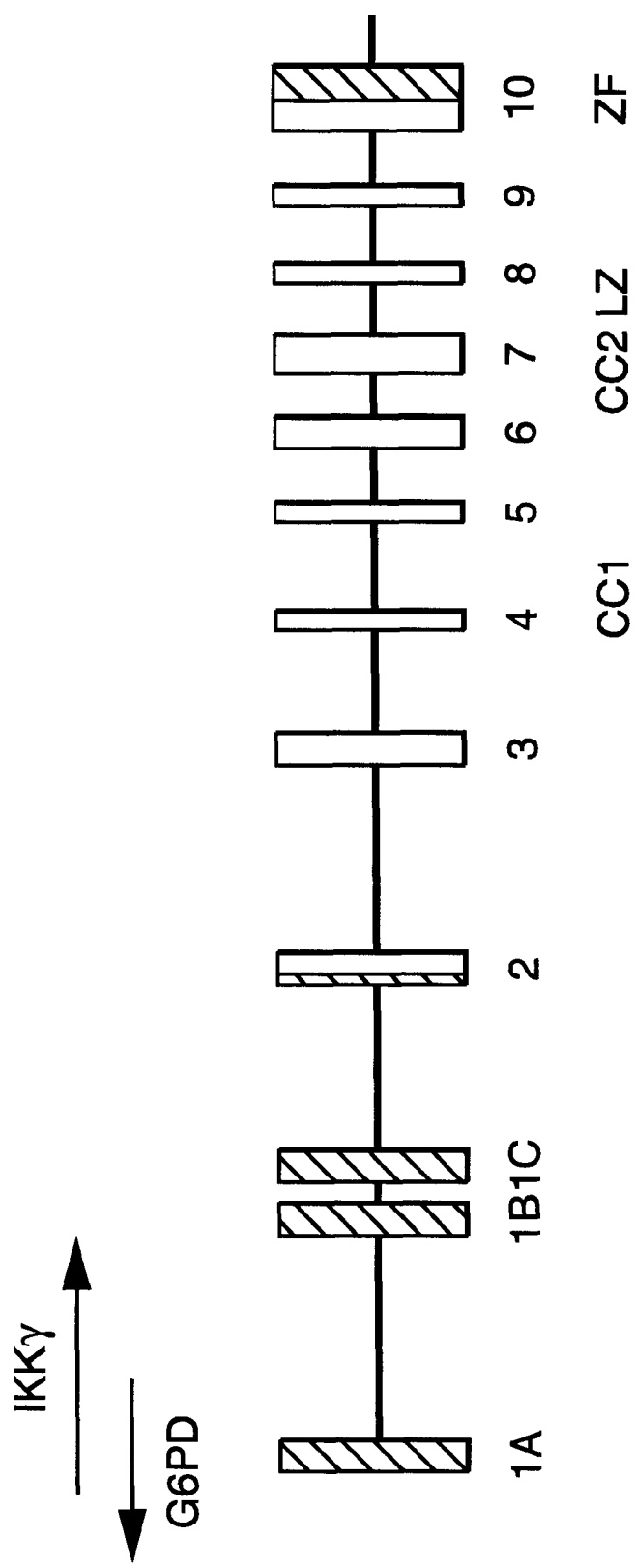
FIGS. 11A–B provides a schematic of the genome organization of the human Ikkγ locus and Ikkγ exon fragments PCR-amplified from wild type and IP genomic DNA templates.
Figure 11B:
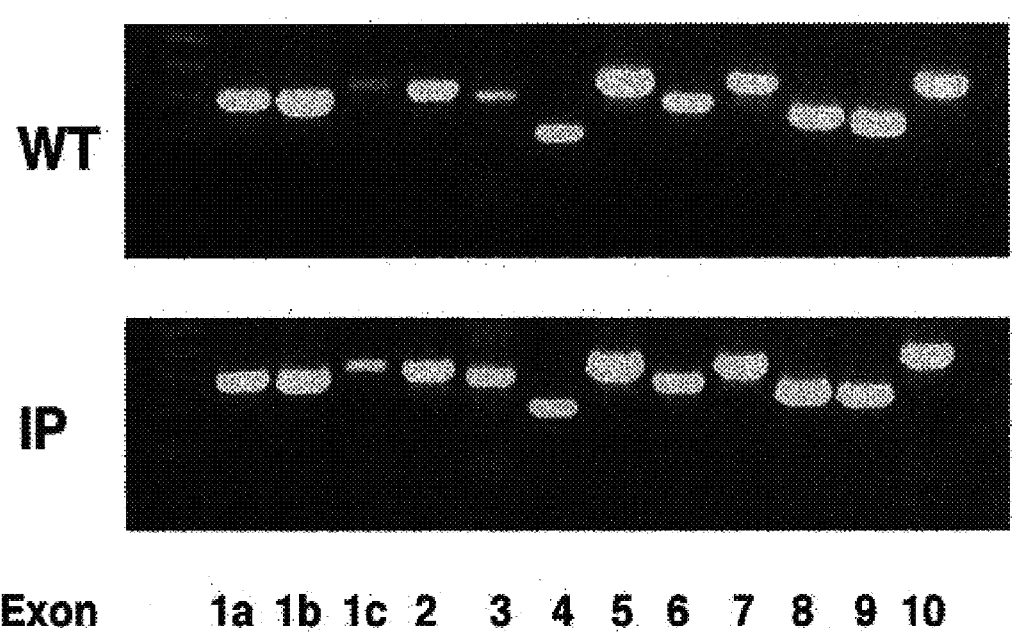

In this Example, the PCR amplification of the Ikkγ exons in a human IP subject is described. The human Ikkγ genomic locus consists of 12 exons, including nine coding and three noncoding exons (Smahi et al., *Nature* 405:466–472 [2000]). All twelve exons were individually amplified by PCR using specific oligonucleotides for each exon. As shown in FIG. 11, all coding and noncoding exons were detected in the genomic DNA isolated from a human IP subject (Makris et al., *Mol. Cell* 5:969–979 [2000]).

EXAMPLE 11

Conformation Sensitive Gel Electrophoresis (CSGE)

Figure 12A:
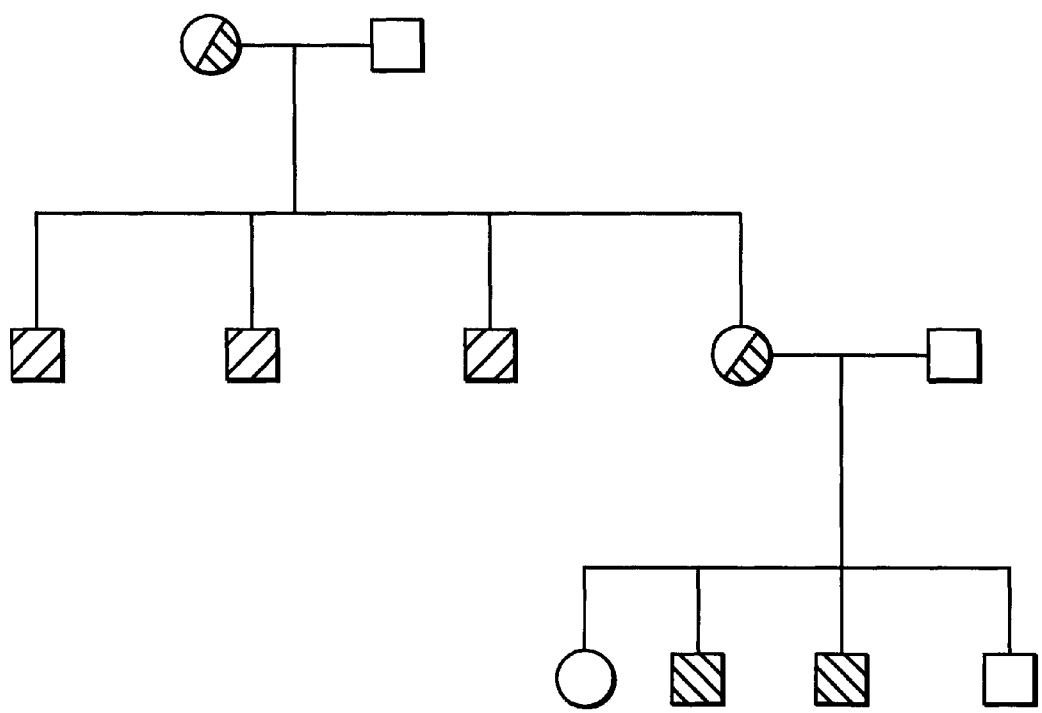
Figure 12B:
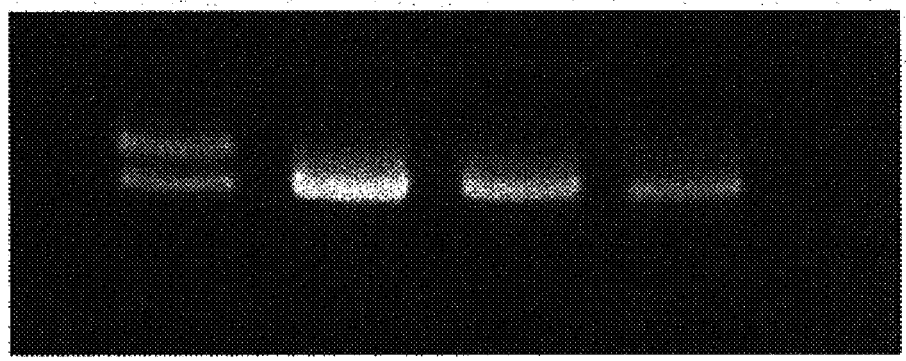

In this Example, the use of CSGE to detect mutations in a human IP family is described. All 12 exons were amplified from genomic DNA isolated from an IP carrier, a healthy son, a wild type fibroblast cell line and an IP fibroblast cell line. The amplified DNA was then subjected to CSGE in order to detect possible mutations. Interestingly, when comparing the mobility of the DNA amplified from the IP carrier and her normal son, differences were observed (See, FIG. 12, Panel B). When this DNA was sequenced, a 13 bp duplication at the end of a cytosine tract was found in exon 10 of the IP carrier. The 13 bp duplication causes a frameshift after amino acid Pro-393 and truncates the protein after the addition of four novel amino acids (See, FIG. 12, Panel C). This mutation located in the putative zinc-finger domain of IKKγ, results in complete removal of the domain and correlates with IP in human females and lethality in human males.

EXAMPLE 12

IKK Activation and NF-κB Binding Activity

Figure 13A:
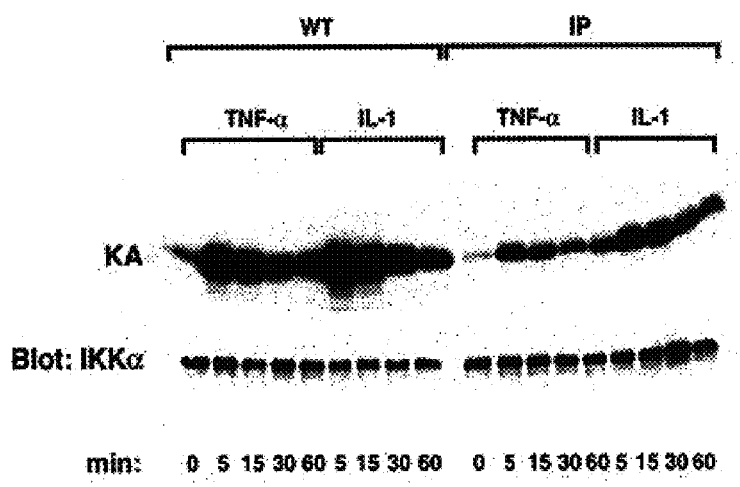
FIGS. 13A–C show results obtained from a biochemical analysis of wild type and IP fibroblasts. Panel A shows that IP fibroblasts exhibit a reduction in cytokine-induced IKK kinase activity, while Panel B shows that IP fibroblasts exhibit a reduction in cytokine-induced NF-κB binding activity. As shown in Panel C, the reduction in IKK kinase and NF-κB binding activities were not due to a lack of p50 or p65 subunits.
Figure 13B:
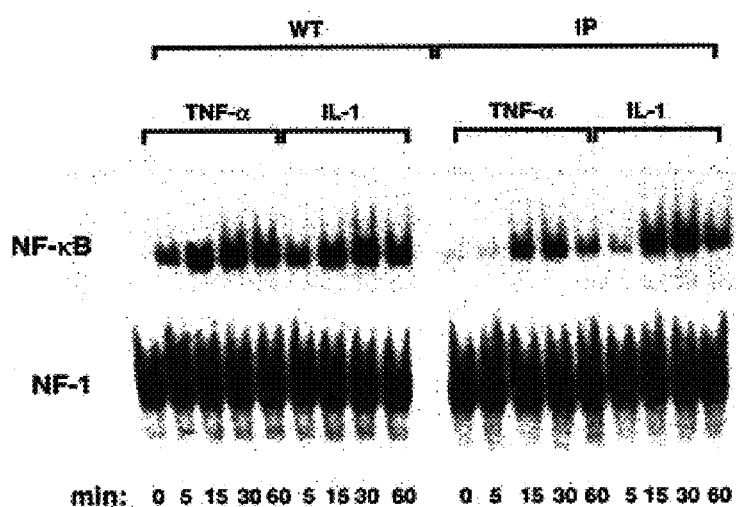
Figure 13C:
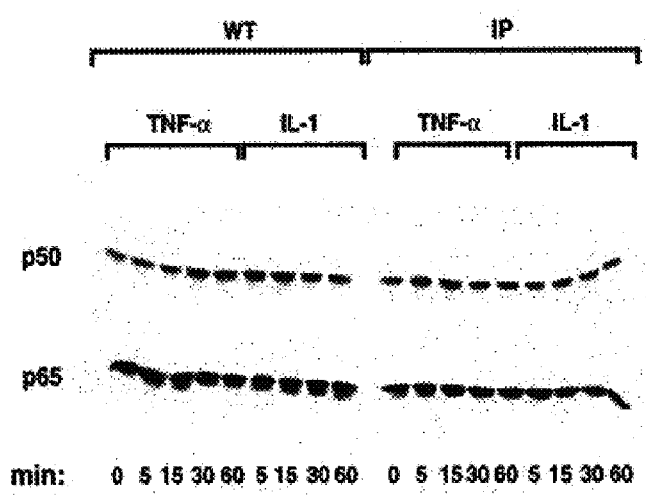

In this example, biochemical analyses of wild type and IP fibroblasts are described. Human wild type and IP fibroblasts were cultured in the presence of the cytokines TNFα and IL-1. A marked reduction in both IKK activation and NF-κB binding activity was observed in IP fibroblasts in which the putative zinc-finger was deleted (See, FIG. 13, Panels A & B). These effects were not due to a lack of p65 or p50 subunits, since both of these family members were expressed to similar levels in wild type and IP fibroblasts (See, FIG. 13, Panel C).

From the above, it should be evident that the present invention describes improved methods and compositions involving IKKγ and IKKγ mutants. In particular, the present invention provides methods and compositions, including transgenic animals, suitable for use in determining means to treat, control, and/or prevent incontinentia pigmenti (IP). The present invention also provides methods to detect the presence of mutations in the IKKγ gene and protein.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the present invention and the following claims.

What is claimed is:

1. A method for detecting a mutant Ikkγ/NEMO gene by detecting protein expression in an individual selected from the group consisting of human and mouse, said method comprising detecting IKKα and IKKβ expression, in the absence of IKKγ/NEMO expression, in biopsy material obtained from said individual.

2. The method of claim 1, wherein said detection is by immunoblot.

3. The method of claim 1, further comprising identifying said individual as having incontinentia pigmenti or as an incontinentia pigmenti carrier.

4. The method of claim 1, wherein said biopsy material comprises cells selected from the group consisting of skin cells, embryonic stem cells, embryonic fibroblast cells, hepatocyte cells, thymocyte cells splenocyte cells, epidermal cells, and fibroblast cells.

5. The method of claim 1, wherein said mutant Ikkγ/NEMO gene comprises a mutation in at least one exon selected from the group consisting of exon 1, exon 2, and exon 10.

6. The method of claim 5, wherein said exon is exon 1.

7. The method of claim 5, wherein said exon is exon 2.

8. The method of claim 5, wherein said exon is exon 10.

9. A method for detecting a mutant Ikkγ/NEMO gene in an animal selected from the group consisting of human and mouse, said method comprising:

(a) detecting a reduced level of IKKγ/NEMO polypeptide in a tissue from said animal compared to the level of IKKγ/NEMO polypeptide in a tissue from a normal animal, and (b) detecting no change in the level of IKKα polypeptide and IKKβ polypeptide in said tissue from said animal compared to the level of IKKα polypeptide and IKKβ polypeptide in said tissue from said normal animal.

10. The method of claim 9, further comprising identifying said animal as having incontinentia pigmenti or as an incontinentia pigmenti carrier.

11. The method of claim 9, wherein said detecting is by immunoblot.

12. The method of claim 9, wherein said tissue from said animal comprises cells selected from the group consisting of skin cells, embryonic stem cells, embryonic fibroblast cells, hepatocyte cells, thymocyte cells splenocyte cells, epidermal cells, and fibroblast cells.

13. The method of claim 9, wherein said mutant Ikkγ/NEMO gene comprises a mutation in at least one exon selected from the group consisting of exon 1, exon 2, and exon 10.

14. The method of claim 13, wherein said exon is exon 1.

15. The method of claim 13, wherein said exon is exon 2.

16. The method of claim 13, wherein said exon is exon 10.

17. A method for detecting a mutant Ikkγ/NEMO gene in an animal selected from the group consisting of human and mouse, said method comprising:

(a) detecting a reduced level of IKKγ/NEMO mRNA in a tissue from said animal compared to the level of IKKγ/NEMO mRNA in a tissue from a normal animal, and (b) detecting no change in the level of IKKα mRNA and IKKβ mRNA in said tissue from said animal compared to the level of IKKα mRNA and IKKβ mRNA in said tissue from said normal animal.

18. The method of claim 17, further comprising identifying said animal as having incontinentia pigmenti or as an incontinentia pigmenti carrier.

19. The method of claim 17, wherein said detecting is by Northern blot.

20. The method of claim 17, wherein said tissue from said animal comprises cells selected from the group consisting of skin cells, embryonic stem cells, embryonic fibroblast cells, hepatocyte cells, thymocyte cells splenocyte cells, epidermal cells, and fibroblast cells.

21. The method of claim 17, wherein said mutant Ikkγ/NEMO gene comprises a mutation in at least one exon selected from the group consisting of exon 1, exon 2, and exon 10.

22. The method of claim 21, wherein said exon is exon 1.

23. The method of claim 21, wherein said exon is exon 2.

24. The method of claim 21, wherein said exon is exon 10.

25. A method for detecting a mutant Ikkγ/NEMO gene in an animal selected from the group consisting of human and mouse, said method comprising detecting a difference in mobility of at least one Ikkγ/NEMO exon in a tissue from said animal compared to mobility of said Ikkγ/NEMO exon in a tissue from a normal animal.

26. The method of claim 25, further comprising identifying said animal as having incontinentia pigmenti or as an incontinentia pigmenti carrier.

27. The method of claim 25, wherein said detecting is by reverse transcriptase polymerase chain reaction (RT-PCR).

28. The method of claim 25, wherein said detecting is by single-stranded conformation polymorphism (SSCP) analysis.

29. The method of claim 25, wherein said detecting is by conformation-sensitive gel electrophoresis (CSGE).

30. The method of claim 25, wherein said tissue from said animal comprises cells selected from the group consisting of skin cells, embryonic stem cells, embryonic fibroblast cells, hepatocyte cells, thymocyte cells splenocyte cells, epidermal cells, and fibroblast cells.

31. The method of claim 25, wherein said mutant Ikkγ/NEMO gene comprises a mutation in at least one exon selected from the group consisting of exon 1, exon 2, and exon 10.

32. The method of claim 31, wherein said exon is exon 1.

33. The method of claim 31, wherein said exon is exon 2.

34. The method of claim 31, wherein said exon is exon 10.

35. The method of claim 25, wherein said detecting is by Southern blot.

* * * * *

UNITED STATES PATENT AND TRADEMARK OFFICE
CERTIFICATE OF CORRECTION

PATENT NO. : 6,689,564 B2  Page 1 of 1
DATED : February 10, 2004
INVENTOR(S) : Makris et al.

It is certified that error appears in the above-identified patent and that said Letters Patent is hereby corrected as shown below:

Column 25,
Lines 19 and 34, please delete "Ikkγ/NEMO" and insert

*--Ikkγ/NEMO--.*

Lines 44 and 46, please delete "IKKγ/NEMO" and insert

*--Ikkγ/NEMO--.*

Column 26,
Lines 20, 40, 47, 50 and 51, please delete "Ikkγ/NEMO" and insert

*--Ikkγ/NEMO--.*

Column 27,
Line 1, please delete "Ikkγ/NEMO" and insert

*--Ikkγ/NEMO--.*

Signed and Sealed this

Thirteenth Day of April, 2004

JON W. DUDAS
*Acting Director of the United States Patent and Trademark Office*

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
tccggttctg tcggagcggt c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic
```

<400> SEQUENCE: 2
acccactcgt gcacccaact g                                      21

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
gagagcatgg agggccat                                          18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
ccactcctct gtgacact                                          18

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
gactagacat gtcttaacat ctgtcc                                 26

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
cctattgcat ggactgcagc ttatg                                  25

<210> SEQ ID NO 7
<211> LENGTH: 30
<212> TYPE: DNA
<213> ORGANISM: Homo sapiens

<400> SEQUENCE: 7
aggagccccc ccgaggagcc acctgacttc                             30

<210> SEQ ID NO 8
<211> LENGTH: 10
<212> TYPE: PRT
<213> ORGANISM: Homo sapiens

<400> SEQUENCE: 8

Arg Ser Pro Pro Glu Glu Pro Pro Asp Phe
1               5                   10

<210> SEQ ID NO 9
<211> LENGTH: 39
<212> TYPE: DNA
<213> ORGANISM: Homo sapiens

```
<400> SEQUENCE: 9
aggagccccc ccgaggagcc accccgagga gccacctga                              39

<210> SEQ ID NO 10
<211> LENGTH: 12
<212> TYPE: PRT
<213> ORGANISM: Homo sapiens

<400> SEQUENCE: 10

Arg Ser Pro Pro Glu Glu Pro Pro Arg Gly Ala Thr
1               5                   10
```